US008771988B2

(12) United States Patent
Goepfert et al.

(10) Patent No.: US 8,771,988 B2
(45) Date of Patent: Jul. 8, 2014

(54) PROTEIN EXPRESSION FROM MULTIPLE NUCLEIC ACIDS

(75) Inventors: Ulrich Goepfert, Munich (DE); Hendrik Knoetgen, Penzberg (DE); Erhard Kopetzki, Penzberg (DE); Anne Stern, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 407 days.

(21) Appl. No.: 12/681,781

(22) PCT Filed: Oct. 9, 2008

(86) PCT No.: PCT/EP2008/008523
§ 371 (c)(1),
(2), (4) Date: Apr. 6, 2010

(87) PCT Pub. No.: WO2009/046978
PCT Pub. Date: Apr. 16, 2009

(65) Prior Publication Data
US 2010/0249379 A1     Sep. 30, 2010

(30) Foreign Application Priority Data
Oct. 12, 2007   (EP) .................................... 07019999

(51) Int. Cl.
*C12P 21/08*    (2006.01)
(52) U.S. Cl.
USPC ........................................ 435/69.6; 435/70.1
(58) Field of Classification Search
None
See application file for complete search history.

(56) References Cited

U.S. PATENT DOCUMENTS

| 4,912,038 | A | 3/1990 | Schilling, Jr. et al. |
| 5,852,175 | A | 12/1998 | Cummings |
| 7,202,072 | B2 | 4/2007 | Mueller et al. |
| 2003/0040047 | A1 | 2/2003 | Farwick et al. |
| 2003/0096341 | A1 | 5/2003 | Mueller et al. |
| 2007/0161079 | A1 | 7/2007 | Reiter et al. |
| 2008/0254513 | A1 | 10/2008 | Cayli |

FOREIGN PATENT DOCUMENTS

| EP | 0481791 | 4/1992 |
| EP | 0569678 | 11/1993 |
| EP | 0659880 | 6/1995 |
| EP | 1482031 | 12/2004 |
| WO | 8900999 | 2/1989 |
| WO | 89/10959 | 11/1989 |
| WO | 93/01296 | 1/1993 |
| WO | 94/25067 | 11/1994 |
| WO | 95/17513 | 6/1995 |
| WO | 99/47647 | 9/1999 |
| WO | 01/38557 | 5/2001 |
| WO | 03/076588 | 9/2003 |
| WO | 2004/083247 | 9/2004 |
| WO | 2004/087758 | 10/2004 |
| WO | 2005/113770 | 12/2005 |
| WO | 2006/072564 | 6/2006 |
| WO | 2007036291 | 4/2007 |
| WO | 2007/109052 | 9/2007 |
| WO | 2007/113172 | 10/2007 |

OTHER PUBLICATIONS

Dorai, H. et al., "Early prediction of instability of CHinese Hamster Ovary cell lines expressing recombinant antibodies and antibody-fusion proteins", Nov. 2011, Biotech. and Bioeng., vol. 109: pp. 1016-1030.*
Lamango, N.S. et al, Arch. Biochem. Biophys 330 (1996) 238-250.
Waldenstroem, M. et al, Gene 120 (1992) 175-181.
Moretto Nadia et al: "Conformation-Sensitive Antibodies Against Alzheimer Amyloid-Beta by Immunization wtih a Thioredoxin-Constrained B-Cell Epitope Peptide" Jour of Biolgoical Chemistry, 282:15 (2007) 11436-11445 XP002451806.
Edmonds et al, 'Development of transfection and high-producer screening protocols for the CHOK1SV cell system,' Mol Biotechnol. Oct. 2006;34(2):179-90., pp. 12.
Link et al., 'Bioprocess development for the production of a recombinant MUC1 fusion protein expressed by CHO-K1 cells in protein-free medium,' vol. 110, Issue 1, May 13, 2004, pp. 51-62., pp. 12.

(Continued)

*Primary Examiner* — Michael Burkhart

(57) ABSTRACT

The current invention reports a method for the recombinant production of a secreted heterologous immunoglobulin in a CHO cell comprising the following steps: i) providing a CHO cell, which is adapted to growth in suspension culture, adapted to growth in serum-free medium, mycoplasma free, and virus free, ii) providing a vector comprising a prokaryotic origin of replication, a first nucleic acid conferring resistance to a prokaryotic selection agent, a second nucleic acid encoding the heavy chain of said heterologous immunoglobulin, a third nucleic acid encoding the light chain of said heterologous immunoglobulin, a fourth nucleic acid conferring resistance to a eukaryotic selection agent, iii) transfecting said CHO cell, wherein said transfecting comprises a) transfecting said CHO cell with said vector comprising a fourth nucleic acid conferring resistance to a first eukaryotic selection agent, b) selecting a CHO cell by growth in cultivation medium containing said first eukaryotic selection agent, c) transfecting said selected CHO cell with said vector comprising a fourth nucleic acid conferring resistance to a second eukaryotic selection agent different to said first eukaryotic selection agent, d) selecting a CHO cell by selected growth in cultivation medium containing said first and said second eukaryotic selection agent, iv) cultivating said transfected CHO cell in a medium in the presence of said first and second eukaryotic selection agent, under conditions suitable for the expression of said second, and third nucleic acid, and v) recovering said secreted heterologous immunoglobulin from the cultivation medium.

11 Claims, 9 Drawing Sheets

(56) References Cited

OTHER PUBLICATIONS

Butler et al., 'Adaptation of mammalian cells to non-ammoniagenic media,' Cytotechnology 1994, vol. 15, Issue 1-3, pp. 87-94., pp. 8.

The extended European Search Report by the European Patent Office, issued on Apr. 17, 2013, in the related European application No. 12170648.5., pp. 13.

The extended European Search Report by the European Patent Office, issued on Apr. 17, 2013, in the European application No. 12191535.9., pp. 12.

Altamirano et al., 'Improvement of CHO Cell Culture Medium Formulation: Simultaneous Substitution of Glucose and Glutamine,' Biotechnol. Prog. 2000, 16, 69-75., pp. 7.

Genzel et al, 'Substitution of glutamine by pyruvate to reduce ammonia formation and growth inhibition of mammalian cells,' Biotechnol Prog. Jan.-Feb. 2005;21(1):58-69., pp. 12.

Li, J. et al., J. Immunol. Metho. 318:113-124 (2007).

(EPO Communication in Corres Appl 08836893.1 May 23, 2012).

* cited by examiner (A)

(B)

US 8,771,988 B2

PROTEIN EXPRESSION FROM MULTIPLE NUCLEIC ACIDS

This application is the National Stage of International Application No. PCT/EP2008/008523, filed Oct. 9, 2008, which claims the benefit of EP 07019999.7 filed Oct. 12, 2007, which is hereby incorporated by reference in its entirety.

The current invention is in the field of polypeptide production. More precisely it is reported the production of an immunoglobulin in a mammalian cell whereby the mammalian cell is transfected with different vectors each comprising an expression cassette for the immunoglobulin of interest.

BACKGROUND OF THE INVENTION

Expression systems for the production of recombinant polypeptides are well-known in the state of the art and are described by, e.g., Marino, M. H., Biopharm. 2 (1989) 18-33; Goeddel, D. V., et al., Methods Enzymol. 185 (1990) 3-7; Wurm, F., and Bernard, A., Curr. Opin. Biotechnol. 10 (1999) 156-159. Polypeptides for use in pharmaceutical applications are preferably produced in mammalian cells such as CHO cells, NS0 cells, SP2/0 cells, COS cells, HEK cells, BHK cells, PER.C6® cells, or the like. The essential elements of an expression plasmid are a prokaryotic plasmid propagation unit, for example for *E. coli*, comprising a prokaryotic origin of replication and a prokaryotic selection marker, an eukaryotic selection marker, and one or more expression cassettes for the expression of the structural gene(s) of interest each comprising a promoter, a structural gene, and a transcription terminator including a polyadenylation signal. For transient expression in mammalian cells a mammalian origin of replication, such as the SV40 Ori or OriP, can be included. As promoter a constitutive or inducible promoter can be selected. For optimized transcription a Kozak sequence may be included in the 5' untranslated region. For mRNA processing, in particular mRNA splicing and transcription termination, mRNA splicing signals, depending on the organization of the structural gene (exon/intron organization), may be included as well as a polyadenylation signal.

Expression of a gene is performed either as transient or as permanent expression. The polypeptide(s) of interest are in general secreted polypeptides and therefore contain an N-terminal extension (also known as the signal sequence) which is necessary for the transport/secretion of the polypeptide through the cell into the extracellular medium. In general, the signal sequence can be derived from any gene encoding a secreted polypeptide. If a heterologous signal sequence is used, it preferably is one that is recognized and processed (i.e. cleaved by a signal peptidase) by the host cell. For secretion in yeast for example the native signal sequence of a heterologous gene to be expressed may be substituted by a homologous yeast signal sequence derived from a secreted gene, such as the yeast invertase signal sequence, alpha-factor leader (including *Saccharomyces, Kluyveromyces, Pichia*, and *Hansenula* α-factor leaders, the second described in U.S. Pat. No. 5,010,182), acid phosphatase signal sequence, or the *C. albicans* glucoamylase signal sequence (EP 0 362 179). In mammalian cell expression the native signal sequence of the protein of interest is satisfactory, although other mammalian signal sequences may be suitable, such as signal sequences from secreted polypeptides of the same or related species, e.g. for immunoglobulins from human or murine origin, as well as viral secretory signal sequences, for example, the herpes simplex glycoprotein D signal sequence. The DNA fragment encoding for such a presegment is ligated in frame to the DNA fragment encoding a polypeptide of interest.

Today CHO cells are widely used for the expression of pharmaceutical polypeptides, either at small scale in the laboratory or at large scale in production processes. Due to their wide distribution and use the characteristic properties and the genetic background of CHO cells is well known. Therefore, CHO cells are approved by regulatory authorities for the production of therapeutic proteins for application to human beings.

In EP 0 569 678 are reported double transfectants of MHC genes as cellular vaccines for immunoprevention of tumor metastasis. WO 97/08342 reports an improved method for measuring the activity of a promoter sequence in a mammalian cell using a reporter gene. The use of anti-RhoA and anti-RhoC siRNAs in order to inhibit specifically RhoA or RhoC synthesis is reported in WO 2005/113770. A method for the recombinant production or expression of eukaryotic alkaline phosphatase mutant in yeast cells is reported in U.S. Pat. No. 7,202,072. WO 2001/038557 reports a method of screening multiply transformed cells using bicistronic expression of fluorescent proteins. A method for producing recombinant eukaryotic cell lines expressing multiple proteins or RNAs of interest is reported in WO 1999/47647. Systems, including methods, compositions, and kits, for transfection of cells with transfection materials using coded carriers are reported in WO 2003/076588. In U.S. Pat. No. 5,089,397 is reported an expression system for recombinant production of a desired protein comprising CHO cells transformed with a DNA sequence having the desired protein coding sequence under the control of the human metallothionein-II promoter. A method for producing recombinant proteins is reported in US 2003/0040047. Lamango et al. (Lamango, N. S., et al., Arch. Biochem. Biophys. 330 (1996) 238-250) report the dependency of the production of prohormone convertase 2 from the presence of the neuroendocrine polypeptide 7B2. The transfection of a BPV-1-based expression vector into cells harboring unintegrated replicating BPV-1 genomes is reported by Waldenstroem, M., et al., Gene 120 (1992) 175-181. U.S. Pat. No. 4,912,038 reports methods and vectors for obtaining canine and human 32K alveolar surfactant protein. In WO 89/10959 are reported recombinant DNA techniques and the expression of mammalian polypeptides in genetically engineered eukaryotic cells. A repeated co-transfer of an expression vector for human growth hormone and an expression vector for a selection marker gene is reported in DD 287531.

SUMMARY OF THE INVENTION

A first aspect of the current invention is a method for the recombinant production of a heterologous immunoglobulin which is secreted to the cultivation medium in a CHO cell comprising:
a) providing a CHO cell, which is
  adapted to growth in suspension culture,
  adapted to growth in serum-free medium,
  mycoplasm free, and
  optional virus free,
b) providing a nucleic acid comprising
  a prokaryotic origin of replication,
  a first nucleic acid sequence conferring resistance to a prokaryotic selection agent,
  a second nucleic acid sequence encoding the heavy chain of said heterologous immunoglobulin, and/or a third nucleic acid sequence encoding the light chain of said heterologous immunoglobulin, whereby a first transfection vector is provided which comprises said provided nucleic acid, which comprises said first as well as said second and/or third nucleic acid, and an additional fourth nucleic acid sequence conferring resistance to a first eukaryotic selection agent, and
whereby a second transfection vector is provided which comprises said provided nucleic acid, which comprises the identical first as well as second and/or third nucleic acid as that/those in said provided nucleic acid contained in the first transfection vector, and an additional fourth nucleic acid sequence conferring resistance to a second eukaryotic selection agent, which is different from the fourth nucleic acid in said first transfection vector, whereby said second eukaryotic selection agent is different from said first eukaryotic selection agent,
c) transfecting said provided CHO cell and selecting said transfected CHO cell with said transfection vectors of step b), wherein said transfecting and selecting comprises the following steps in the following order:
  (i) transfecting said CHO cell with said first transfection vector,
  (ii) selecting a CHO cell transfected in (i) by selected growth in a cultivation medium containing said first eukaryotic selection agent to which the first transfection vector confers resistance,
  (iii) transfecting said CHO cell selected in (ii) with said second transfection vector,
  (iv) selecting a CHO cell transfected in (iii) by selected growth in a cultivation medium containing said first eukaryotic selection agent, to which said first transfection vector confers resistance, and containing said second eukaryotic selection agent, to which said second transfection vector confers resistance,
d) cultivating said transfected and selected CHO cell of step c) in a medium containing said first and second eukaryotic selection agent under conditions suitable for the expression of said second and/or third nucleic acid,
e) recovering said secreted heterologous immunoglobulin from the cultivation medium and thereby producing a heterologous immunoglobulin in a CHO cell, which immunoglobulin is secreted to the cultivation medium.

In one embodiment of the method according to the invention said CHO cell is a CHO K1 cell, or a CHO DG44 cell, or a CHO XL99 cell, or a CHO DXB11 cell, or a CHO DP12 cell. In another embodiment the promoter employed for the transcription of said second and third nucleic acids is different from the promoter employed for the transcription of said fourth nucleic acid. A further embodiment is that the promoter employed for the transcription of said second and third nucleic acids is the same. In one embodiment said promoter employed for the transcription of said second and third nucleic acid is the CMV promoter. In another embodiment said promoter employed for the transcription of said fourth nucleic acid is the SV40 promoter. In one embodiment said heterologous immunoglobulin is an anti-Aβ antibody. Exemplary anti-Aβ antibodies are reported e.g. in WO 2003/070760.

In one embodiment said selecting a transfected CHO cell in step c) (ii) and/or (iv) is by growth in cultivation medium without a selection agent for 10 to 72 hours followed by selected growth in a cultivation medium containing said first eukaryotic selection agent in case of (ii) or said first and second eukaryotic selection agent in case of (iv).

In still a further embodiment the codon usage of said second and third nucleic acid is optimized for the translation in CHO cells. Also an embodiment is that said second and/or third nucleic acid contains an intronic nucleic acid sequence.

Another embodiment comprises that said first transfection vector and said second transfection vector differ only in the nucleic acid conferring resistance to said eukaryotic selection agent, i.e. in said fourth nucleic acid, and are otherwise at least 95% identical based on the nucleic acid sequence. In another embodiment said transfection vectors differ each only in the nucleic acid conferring resistance to said first, second, and third eukaryotic selection agent.

In one embodiment said method further comprises:
after step b) a step b1):
b1) providing a nucleic acid comprising
  a prokaryotic origin of replication,
  a first nucleic acid sequence conferring resistance to a prokaryotic selection agent,
  a second nucleic acid sequence encoding the heavy chain of said heterologous immunoglobulin, and/or a third nucleic acid sequence encoding the light chain of said heterologous immunoglobulin,
  whereby a third transfection vector is provided which comprises said provided nucleic acid, which comprises the identical frist as well as second and/or third nucleic acid as that/those in said provided nucleic acid contained in the first and second transfection vector, and an additional fourth nucleic acid sequence conferring resistance to a third eukaryotic selection agent, which is different from the fourth nucleic acid in said first and second transfection vector, whereby said third eukaryotic selection agent is different from said first eukaryotic selection agent and is also different from said second eukaryotic selection agent,
and further comprises after step c) (iv) the following steps (v) and (vi)
  (v) transfecting said CHO cell selected in (iv) with said third transfection vector,
  (vi) selecting a CHO cell transfected in (v) by selected growth in cultivation medium containing said first eukaryotic selection agent to which the first transfection vector confers resistance and said second eukaryotic selection agent to which the second transfection vector confers resistance and said third eukaryotic selection agent to which the third transfection vector confers resistance,
and further said medium for cultivating said transfected CHO cell in step d) comprises said first, second, and third eukaryotic selection agent.

In one embodiment said selecting a CHO cell transfected in step c) (vi) is by growth in cultivation medium without a selection agent for 10 to 72 hours followed by selected growth in a cultivation medium containing said first and second and third eukaryotic selection agent.

In another embodiment the method according to the invention comprises a further step
f) purifying said recombinantly produced and recovered heterologous immunoglobulin of step e) with one or more chromatographic steps.

One embodiment is that said step c) and said step d) are performed in the same medium. Still another embodiment is that said medium is a serum-free medium, or a serum-free medium supplemented with defined animal-derived components, or an animal-derived component free medium, or a protein-free medium, or a chemically defined medium, or a defined protein-free medium. In a further embodiment in said step d) is said cultivating in the presence of said eukaryotic selection agents in a volume of less than 500 liter and said cultivating is in the absence of said eukaryotic selection agents in a volume of 500 liter or more, whereby said recovering said secreted heterologous immunoglobulin is from the cultivation medium without said eukaryotic selection agents. In a further embodiment said cultivating in said step d) is comprising sequential cultivations each with increasing cultivation volume up to a preset final cultivation volume, whereby the cultivations are performed in the presence of said eukaryotic selection agents up to a cultivation volume of 1% (v/v) of the cultivation volume of the final cultivation and in the absence of said eukaryotic selection agents in a cultivation volume of more than 1% (v/v) of the cultivation volume of the final cultivation.

The productivity of said CHO cells is in one embodiment over 40 generations not less than 70% and not more than 130% of the productivity after 10 generations of cultivation as split-batch cultivation. In another embodiment is the productivity of said CHO cells over 60 generations not less than 50% and not more than 150% of the productivity after 10 generations of cultivation as split-batch cultivation. In still a further embodiment is the productivity of said CHO cell at least 1.5 g/l of said heterologous immunoglobulin within 21 days as fed-batch cultivation.

A second aspect of the current invention is a CHO cell obtainable with the following method:
a) providing a CHO cell, which is
  adapted to growth in suspension culture,
  adapted to growth in serum-free medium,
  mycoplasma free, and
  optional virus free,
b) providing a nucleic acid comprising
  a prokaryotic origin of replication,
  a first nucleic acid sequence conferring resistance to a prokaryotic selection agent,
  a second nucleic acid sequence encoding the heavy chain of a heterologous immunoglobulin, and/or a third nucleic acid sequence encoding the light chain of a heterologous immunoglobulin,
  whereby a first transfection vector is provided which comprises said provided nucleic acid, which comprises said frist as well as second and/or third nucleic acid, and an additional fourth nucleic acid sequence conferring resistance to a first eukaryotic selection agent, and
  whereby a second transfection vector is provided which comprises said provided nucleic acid, which comprises the identical frist as well as second and/or third nucleic acid as that/those in said provided nucleic acid contained in the first transfection vector, and an additional fourth nucleic acid sequence conferring resistance to a second eukaryotic selection agent, which is different from the fourth nucleic acid in said first transfection vector, whereby said second eukaryotic selection agent is different from said first eukaryotic selection agent,
c) transfecting said CHO cell, wherein said transfecting comprises the following steps in the following order:
  (i) transfecting said CHO cell with said first transfection vector,
  (ii) selecting a CHO cell transfected in (i) by selected growth in cultivation medium containing a first eukaryotic selection agent to which the first transfection vector confers resistance,
  (iii) transfecting said CHO cell selected in (ii) with said second transfection vector,
  (iv) selecting a CHO cell transfected in (iii) by selected growth in cultivation medium containing said first eukaryotic selection agent to which the first transfection vector confers resistance and said second eukaryotic selection agent to which the second transfection vector confers resistance.

DETAILED DESCRIPTION OF THE INVENTION

Methods and techniques known to a person skilled in the art, which are useful for carrying out the current invention, are described e.g. in Ausubel, F. M., ed., Current Protocols in Molecular Biology, Volumes I to III (1997), Wiley and Sons; Sambrook, et al., Molecular Cloning: A Laboratory Manual, Second Edition, Cold Spring Harbor Laboratory Press, Cold Spring Harbor, N.Y. (1989).

General chromatographic methods and their use are known to a person skilled in the art. See for example, Chromatography, $5^{th}$ edition, Part A: Fundamentals and Techniques, Heftmann, E. (ed), Elsevier Science Publishing Company, New York, (1992); Advanced Chromatographic and Electromigration Methods in Biosciences, Deyl, Z. (ed.), Elsevier Science BV, Amsterdam, The Netherlands, (1998); Chromatography Today, Poole, C. F., and Poole, S. K., Elsevier Science Publishing Company, New York, (1991); Scopes, Protein Purification: Principles and Practice (1982); Sambrook, J., et al. (ed), Molecular Cloning: A Laboratory Manual, Second Edition, Cold Spring Harbor Laboratory Press, Cold Spring Harbor, N.Y., 1989; or Current Protocols in Molecular Biology, Ausubel, F. M., et al. (eds), John Wiley & Sons, Inc., New York.

For the purification of recombinantly produced heterologous immunoglobulins often a combination of different column chromatography steps is employed. Generally a Protein A affinity chromatography is followed by one or two additional separation steps. The final purification step is a so called "polishing step" for the removal of trace impurities and contaminants like aggregated immunoglobulins, residual HCP (host cell protein), DNA (host cell nucleic acid), viruses, or endotoxins. For this polishing step often an anion exchange material in a flow-through mode is used.

Different methods are well established and widespread used for protein recovery and purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

The term "amino acid" as used within this application denotes the group of carboxy α-amino acids, which directly or in form of a precursor can be encoded by a nucleic acid. The individual amino acids are encoded by nucleic acids consisting of three nucleotides, so called codons or base-triplets. Each amino acid is encoded by at least one codon. The encoding of the same amino acid by different codons is known as "degeneration of the genetic code". The term "amino acid" as used within this application denotes the naturally occurring carboxy α-amino acids and is comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

A "nucleic acid" or a "nucleic acid sequence", which terms are used interchangeably within this application, refers to a polymeric molecule consisting of individual nucleotides (also called bases) a, c, g, and t (or u in RNA), for example to DNA, RNA, or modifications thereof. This polynucleotide molecule can be a naturally occurring polynucleotide molecule or a synthetic polynucleotide molecule or a combination of one or more naturally occurring polynucleotide molecules with one or more synthetic polynucleotide molecules. Also encompassed by this definition are naturally occurring polynucleotide molecules in which one or more nucleotides are changed (e.g. by mutagenesis), deleted, or added. A nucleic acid can either be isolated, or integrated in another nucleic acid, e.g. in an expression cassette, a plasmid, or the chromosome of a host cell. A nucleic acid is characterized by its nucleic acid sequence consisting of individual nucleotides.

To a person skilled in the art procedures and methods are well known to convert an amino acid sequence, e.g. of a polypeptide, into a corresponding nucleic acid sequence encoding this amino acid sequence. Therefore, a nucleic acid is characterized by its nucleic acid sequence consisting of individual nucleotides and likewise by the amino acid sequence of a polypeptide encoded thereby.

A "polypeptide" is a polymer consisting of amino acids joined by peptide bonds, whether produced naturally or synthetically. Polypeptides of less than about 20 amino acid residues may be referred to as "peptides", whereas molecules consisting of two or more polypeptides or comprising one polypeptide of more than 100 amino acid residues may be referred to as "proteins". A polypeptide may also comprise non-amino acid components, such as carbohydrate groups, metal ions, or carboxylic acid esters. The non-amino acid components may be added by the cell, in which the polypeptide is expressed, and may vary with the type of cell. Polypeptides are defined herein in terms of their amino acid backbone structure or the nucleic acid encoding the same. Additions such as carbohydrate groups are generally not specified, but may be present nonetheless.

The term "immunoglobulin" encompasses the various forms of immunoglobulin structures including complete immunoglobulins and immunoglobulin conjugates. The immunoglobulin employed in the current invention is preferably a human antibody, or a humanized antibody, or a chimeric antibody, or a T cell antigen depleted antibody (see e.g. WO 98/33523, WO 98/52976, and WO 00/34317). Genetic engineering of antibodies is e.g. described in Morrison, S. L., et al., Proc. Natl. Acad. Sci. USA 81 (1984) 6851-6855; U.S. Pat. Nos. 5,202,238 and 5,204,244; Riechmann, L., et al., Nature 332 (1988) 323-327; Neuberger, M. S., et al., Nature 314 (1985) 268-270; Lonberg, N., Nat. Biotechnol. 23 (2005) 1117-1125. Immunoglobulins may exist in a variety of formats, including, for example, Fv, Fab, and F(ab)$_2$ as well as single chains (scFv) or diabodies (e.g. Huston, J. S., et al., Proc. Natl. Acad. Sci. USA 85 (1988) 5879-5883; Bird, R. E., et al., Science 242 (1988) 423-426; in general, Hood et al., Immunology, Benjamin N.Y., 2nd edition (1984); and Hunkapiller, T. and Hood, L., Nature 323 (1986) 15-16).

The term "complete immunoglobulin" denotes an immunoglobulin which comprises two so called light chains and two so called heavy chains. Each of the heavy and light chains of a complete immunoglobulin contains a variable domain (variable region) (generally the amino terminal portion of the polypeptide chain) comprising binding regions that are able to interact with an antigen. Each of the heavy and light chains of a complete immunoglobulin comprises a constant region (generally the carboxyl terminal portion). The constant region of the heavy chain mediates the binding of the antibody i) to cells bearing a Fc gamma receptor (FcγR), such as phagocytic cells, or ii) to cells bearing the neonatal Fc receptor (FcRn) also known as Brambell receptor. It also mediates the binding to some factors including factors of the classical complement system such as component (C1q). The variable domain of an immunoglobulin's light or heavy chain in turn comprises different segments, i.e. four framework regions (FR) and three hypervariable regions (CDR).

The term "immunoglobulin conjugate" denotes a polypeptide comprising at least one domain of an immunoglobulin heavy or light chain conjugated via a peptide bond to a further polypeptide. The further polypeptide is a non-immunoglobulin peptide, such as a hormone, or growth receptor, or antifusogenic peptide, or complement factor, or the like. Exemplary immunoglobulin conjugates are reported in WO 2007/045463.

The term "heterologous immunoglobulin" denotes an immunoglobulin which is not naturally produced by a mammalian cell or the host cell. The immunoglobulin produced according to the method of the invention is produced by recombinant means. Such methods are widely known in the state of the art and comprise protein expression in eukaryotic cells with subsequent recovery and isolation of the heterologous immunoglobulin, and usually purification to a pharmaceutically acceptable purity. For the production, i.e. expression, of an immunoglobulin a nucleic acid encoding the light chain and a nucleic acid encoding the heavy chain are inserted each into an expression cassette by standard methods. Nucleic acids encoding immunoglobulin light and heavy chains are readily isolated and sequenced using conventional procedures. Hybridoma cells can serve as a source of such nucleic acids. The expression cassettes may be inserted into an expression plasmid(s), which is (are) then transfected into host cells, which do not otherwise produce immunoglobulins. Expression is performed in appropriate prokaryotic or eukaryotic host cells and the immunoglobulin is recovered from the cells after lysis or from the culture supernatant.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e. at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

"Heterologous DNA" or "heterologous polypeptide" refers to a DNA molecule or a polypeptide, or a population of DNA molecules or a population of polypeptides, that do not exist naturally within a given host cell. DNA molecules heterologous to a particular host cell may contain DNA derived from the host cell species (i.e. endogenous DNA) so long as that host DNA is combined with non-host DNA (i.e. exogenous DNA). For example, a DNA molecule containing a non-host DNA segment encoding a polypeptide operably linked to a host DNA segment comprising a promoter is considered to be a heterologous DNA molecule. Conversely, a heterologous DNA molecule can comprise an endogenous structural gene operably linked with an exogenous promoter. A peptide or polypeptide encoded by a non-host DNA molecule is a "heterologous" peptide or polypeptide.

The term "cell" or "host cell" refers to a cell into which a nucleic acid, e.g. encoding a heterologous polypeptide, can be or is transfected. The term "cell" includes both prokaryotic cells, which are used for propagation of plasmids, and eukaryotic cells, which are used for the expression of a nucleic acid and production of the encoded polypeptide. In one embodiment, the eukaryotic cells are mammalian cells. In another embodiment the mammalian cell is a CHO cell, preferably a CHO K1 cell (ATCC CCL-61 or DSM ACC 110), or a CHO DG44 cell (also known as CHO-DHFR[−], DSM ACC 126), or a CHO XL99 cell, a CHO-T cell (see e.g. Morgan, D., et al., Biochemistry 26 (1987) 2959-2963), or a CHO-S cell, or a Super-CHO cell (Pak, S. C. O., et al. Cytotechnology. 22 (1996) 139-146). If these cells are not adapted to growth in serum-free medium or in suspension an adaptation prior to the use in the current method is to be performed. As used herein, the expression "cell" includes the subject cell and its progeny. Thus, the words "transformant" and "transformed cell" include the primary subject cell and cultures derived there from without regard for the number of transfers or subcultivations. It is also understood that all progeny may not be precisely identical in DNA content, due to deliberate or inadvertent mutations. Variant progeny that have the same function or biological activity as screened for in the originally transformed cell are included.

The term "expression" as used herein refers to transcription and/or translation processes occurring within a cell. The level of transcription of a nucleic acid sequence of interest in a cell can be determined on the basis of the amount of corresponding mRNA that is present in the cell. For example, mRNA transcribed from a sequence of interest can be quantitated by RT-PCR or by Northern hybridization (see Sambrook, et al., 1989, supra). Polypeptides encoded by a nucleic acid of interest can be quantitated by various methods, e.g. by ELISA, by assaying for the biological activity of the polypeptide, or by employing assays that are independent of such activity, such as Western blotting or radioimmunoassay, using immunoglobulins that recognize and bind to the polypeptide (see Sambrook, et al., 1989, supra).

An "expression cassette" refers to a construct that contains the necessary regulatory elements, such as promoter and polyadenylation site, for expression of at least the contained nucleic acid in a cell.

A "transfection vector" is a nucleic acid (also denoted as nucleic acid molecule) providing all required elements for the expression of the in the transfection vector comprised coding nucleic acids/structural gene(s) in a host cell. A transfection vector comprises a prokaryotic plasmid propagation unit, e.g. for *E. coli*, in turn comprising a prokaryotic origin of replication, and a nucleic acid conferring resistance to a prokaryotic selection agent, further comprises the transfection vector one or more nucleic acid(s) conferring resistance to an eukaryotic selection agent, and one or more nucleic acid encoding a polypeptide of interest. Preferably are the nucleic acids conferring resistance to a selection agent and the nucleic acid(s) encoding a polypeptide of interest placed each within an expression cassette, whereby each expression cassette comprises a promoter, a coding nucleic acid, and a transcription terminator including a polyadenylation signal. Gene expression is usually placed under the control of a promoter, and such a structural gene is said to be "operably linked to" the promoter. Similarly, a regulatory element and a core promoter are operably linked if the regulatory element modulates the activity of the core promoter.

A "promoter" refers to a polynucleotide sequence that controls transcription of a gene/structural gene or nucleic acid sequence to which it is operably linked. A promoter includes signals for RNA polymerase binding and transcription initiation. The promoter(s) used will be functional in the cell type of the host cell in which expression of the selected sequence is contemplated. A large number of promoters including constitutive, inducible and repressible promoters from a variety of different sources, are well known in the art (and identified in databases such as GenBank) and are available as or within cloned polynucleotides (from, e.g., depositories such as ATCC as well as other commercial or individual sources). A "promoter" comprises a nucleotide sequence that directs the transcription of an operably linked structural gene. Typically, a promoter is located in the 5' non-coding or untranslated region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee, R. E., et al., Mol. Endocrinol. 7 (1993) 551-560), cyclic AMP response elements (CREs), serum response elements (SREs; Treisman, R., Seminars in Cancer Biol. 1 (1990) 47-58), glucocorticoid response elements (GREs), and binding sites for other transcription factors, such as CRE/ATF (O'Reilly, M. A., et al., J. Biol. Chem. 267 (1992) 19938-19943), AP2 (Ye, J., et al., J. Biol. Chem. 269 (1994) 25728-25734), SP1, cAMP response element binding protein (CREB; Loeken, M. R., Gene Expr. 3 (1993) 253-264) and octamer factors (see, in general, Watson et al., eds., Molecular Biology of the Gene, 4th ed. (The Benjamin/Cummings Publishing Company, Inc. 1987), and Lemaigre, F. P. and Rousseau, G. G., Biochem. J. 303 (1994) 1-14). Among the eukaryotic promoters that have been identified as strong promoters for high-level expression are the SV40 early promoter, adenovirus major late promoter, mouse metallothionein-I promoter, Rous sarcoma virus long terminal repeat, Chinese hamster elongation factor 1 alpha (CHEF-1, see e.g. U.S. Pat. No. 5,888,809), human EF-1 alpha, ubiquitin, and human cytomegalovirus immediate early promoter (CMV IE).

The "promoter" can be constitutive or inducible. An enhancer (i.e., a cis-acting DNA element that acts on a promoter to increase transcription) may be necessary to function in conjunction with the promoter to increase the level of expression obtained with a promoter alone, and may be included as a transcriptional regulatory element. Often, the polynucleotide segment containing the promoter will include enhancer sequences as well (e.g., CMV or SV40).

An "enhancer", as used herein, refers to a polynucleotide sequence that enhances transcription of a gene or coding sequence to which it is operably linked. Unlike promoters, enhancers are relatively orientation and position independent and have been found 5' or 3' (Lusky, M., et al., Mol. Cell Bio., 3 (1983) 1108-1122) to the transcription unit, within an intron (Banerji, J., et al., Cell, 33 (1983) 729-740) as well as within the coding sequence itself (Osborne, T. F., et al., Mol. Cell. Bio., 4 (1984) 1293-1305). Therefore, enhancers may be placed upstream or downstream from the transcription initiation site or at considerable distances from the promoter, although in practice enhancers may overlap physically and functionally with promoters. A large number of enhancers, from a variety of different sources are well known in the art (and identified in databases such as GenBank) and are available as or within cloned polynucleotide sequences (from, e.g., depositories such as the ATCC as well as other commercial or individual sources). A number of polynucleotides comprising promoter sequences (such as the commonly-used CMV promoter) also comprise enhancer sequences. For example, all of the strong promoters listed above may also contain strong enhancers (see e.g. Bendig, M., M., Genetic Engineering 7 (Academic Press, 1988) 91-127).

A "nucleic acid conferring resistance to a selection agent" is a nucleic acid that allows cells carrying it to be specifically selected for or against, in the presence of a selection agent. Such a nucleic acid is also denoted as selection marker. Typically, a selection marker will confer resistance to a selection agent (drug) or compensate for a metabolic or catabolic defect in the host cell. A selection marker can be positive, negative, or bifunctional. A useful positive selection marker is an antibiotic resistance gene. This selection marker allows cells transformed therewith to be positively selected for in the presence of the corresponding selection agent, i.e. under selected growth in the presence e.g. of the corresponding antibiotic. A non-transformed cell is not capable to grow or survive under the selective growth conditions, i.e. in the presence of the selection agent, in culture. Positive selection markers allow selection for cells carrying the marker, whereas negative selection markers allow cells carrying the marker to be selectively eliminated. Eukaryotic selection markers include, e.g., the genes for aminoglycoside phosphotransferase (APH) (conferring resistance to the selection agents such as e.g. hygromycin (hyg), neomycin (neomycin phosphotransferase II, neo), and G418), dihydrofolate reductase (DHFR) (conferring resistance to the selection agent methotrexate), thymidine kinase (tk), glutamine synthetase (GS), asparagine synthetase, tryptophan synthetase (conferring resistance to the selection agent indole), histidinol dehydrogenase (conferring resistance to the selection agent histidinol D), cytidine deaminase, adenosine deaminase and nucleic acids conferring resistance to puromycin, bleomycin, phleomycin, chloramphenicol, Zeocin, and mycophenolic acid. Further selection marker nucleic acids are reported e.g. in WO 92/08796 and WO 94/28143. Prokaryotic selection markers include, e.g. the beta-lactamase gene (conferring resistance to the selection agent ampicillin).

Expression of a gene is performed either as transient or as permanent expression. The polypeptide(s) of interest are in general secreted polypeptides and therefore contain an N-terminal extension (also known as the signal sequence) which is necessary for the transport/secretion of the polypeptide through the cell wall into the extracellular medium. In general, the signal sequence can be derived from any gene encoding a secreted polypeptide. If a heterologous signal sequence is used, it preferably is one that is recognized and processed (i.e. cleaved by a signal peptidase) by the host cell. For secretion in yeast for example the native signal sequence of a heterologous gene to be expressed may be substituted by a homologous yeast signal sequence derived from a secreted gene, such as the yeast invertase signal sequence, alpha-factor leader (including *Saccharomyces, Kluyveromyces, Pichia,* and *Hansenula* α-factor leaders, the second described in U.S. Pat. No. 5,010,182), acid phosphatase signal sequence, or the *C. albicans* glucoamylase signal sequence (EP 0 362 179). In mammalian cell expression the native signal sequence of the protein of interest is satisfactory, although other mammalian signal sequences may be suitable, such as signal sequences from secreted polypeptides of the same or related species, e.g. for immunoglobulins from human or murine origin, as well as viral secretory signal sequences, for example, the herpes simplex glycoprotein D signal sequence. The DNA fragment encoding for such a presegment is ligated in frame, i.e. operably linked, to the DNA fragment encoding a polypeptide of interest.

The first aspect of the current invention is a method for the recombinant production of a secreted heterologous immunoglobulin in a CHO cell which comprises:
a) providing a CHO cell, which is adapted to growth in suspension culture, adapted to growth in serum-free medium, and mycoplasma free;
b) providing a transfection vector, which comprises the following elements:
   a prokaryotic origin of replication,
   a first nucleic acid sequence conferring resistance to a prokaryotic selection agent,
   a second nucleic acid sequence encoding the heavy chain of said heterologous immunoglobulin and a third nucleic acid sequence encoding the light chain of said heterologous immunoglobulin,
   a fourth nucleic acid sequence conferring resistance to a eukaryotic selection agent,
   whereby each of said first to fourth nucleic acid sequence is contained in an expression cassette,
c) transfecting and selecting said CHO cell, wherein said transfecting and selecting comprises the following steps in the following order:
   (i) transfecting said CHO cell with a transfection vector comprising said first to third nucleic acid and a fourth nucleic acid sequence conferring resistance to a first eukaryotic selection agent,
   (ii) selecting a CHO cell transfected in (i) by selected growth in cultivation medium containing said first eukaryotic selection agent,
   (iii) transfecting said CHO cell selected in (ii) with a transfection vector comprising said first to third nucleic acid and a fourth nucleic acid sequence different from that in the transfection vector used in (i) conferring resistance to a second eukaryotic selection agent different to said first eukaryotic selection agent,
   (iv) selecting a CHO cell transfected in (iii) by selected growth in cultivation medium containing said first and said second eukaryotic selection agent,
d) cultivating said transfected and selected CHO cell of step c) in a cultivation medium containing said first and second eukaryotic selection agent, under conditions suitable for the expression of said second, and third nucleic acid,
e) recovering said secreted heterologous immunoglobulin from the cultivation medium and thereby recombinantly producing a heterologous immunoglobulin.

The method according to the invention is suited for the production of a secreted heterologous immunoglobulin in large scale, i.e. industrially. The cultivation of a cell for the production of a desired polypeptide in large scale generally consists of a sequence of individual cultivations, wherein all cultivations except the final, i.e. the large scale, cultivation, i.e. the last one in the sequence, are performed until a certain cell density is reached in the culture vessel. If the predetermined cell density is reached the entire cultivation or a fraction thereof is used to inoculate the next cultivation vessel, which has a larger volume, up to 1000 times the volume of the preceding cultivation. All cultivations which serve as a basis for at least one further cultivation in a larger volume are denoted as seed train fermentations. Only in the large scale cultivation, i.e. in the cultivation which is not intended to serve as the basis for a further cultivation in a larger volume, which is also denoted as main fermentation, is the endpoint of the cultivation determined depending on the concentration of the produced secreted heterologous immunoglobulin in the cultivation medium. The term "large scale" as used within this application denotes the final cultivation of an industrial production process. Preferably a large scale cultivation is performed at a volume of at least 100 l, more preferably of at least 500 l, most preferably of at least 1000 l up to a volume of 20,000 l. In one embodiment the final, i.e. large scale, cultivation medium does not contain a eukaryotic selection agent.

In one embodiment the cultivation of said transfected CHO cell is performed in the presence of said eukaryotic selection agent in a volume of less than 500 liter and the cultivation of said transfected CHO cell is performed in the absence of said eukaryotic selection agents in a volume of 500 liter or more and that said recovering said secreted heterologous immunoglobulin is from the cultivation medium without said eukaryotic selection agents. In a further embodiment the cultivation is comprising sequential cultivations with increasing cultivation volume up to a final cultivation volume, whereby the cultivations are performed in the presence of said eukaryotic selection agents up to a cultivation volume of 1% (v/v) of the cultivation volume of the final or main cultivation and in the absence of all of said eukaryotic selection agents in a cultivation volume of more than 1% (v/v) of the cultivation volume of the final cultivation. In a further embodiment said cultivation is comprising sequential seed train cultivations with increasing cultivation volume, whereby each of the seed train cultivations is performed in the presence of said eukaryotic selection agents and the main fermentation is performed in the absence of all of said eukaryotic selection agents. In one embodiment the cultivation of said transfected CHO cell is performed in the presence of said eukaryotic selection agent in the seed train fermentations and the cultivation of said transfected CHO cell is performed in the absence of said eukaryotic selection agents in the main fermentation and that said recovering said secreted heterologous immunoglobulin is from the main cultivation medium not containing said eukaryotic selection agents. In these embodiments the eukaryotic selection agents are added during the growth phase and omitted during the production phase of said CHO cell. The term "production phase" denotes the cultivation of a CHO cell in a large volume, i.e. the main fermentation, after which the produced heterologous immunoglobulin is recovered.

In another embodiment of the method according to the invention the productivity of said CHO cell is over 40 generations not less than 70% and not more than 130% of the productivity after 10 generations of cultivation as split-batch cultivation. In an embodiment the productivity of said CHO cells is over 60 generations not less than 50% and not more than 150% of the productivity after 10 generations of cultivation as split-batch cultivation. The productivity of said CHO cell is at least 1.5 g/l of said heterologous immunoglobulin within 21 days as fed-batch cultivation in another embodiment. In one embodiment the specific productivity of the CHO cell obtained with the method according to the invention is more than 1 $\mu g/10^6$ cells/d, more than 5 $\mu g/10^6$ cells/d, or more than 10 $\mu g/10^6$ cells/d. In one embodiment the secreted heterologous immunoglobulin is a completely processed secreted heterologous immunoglobulin. The term "completely processed secreted heterologous immunoglobulin" denotes an immunoglobulin i) which is secreted to the cultivation medium and whose signal sequences has been cleaved, ii) which comprises an antigen binding region, iii) which has secondary modifications, such as attached saccharides or polysaccharides, and/or correctly formed disulfide bonds.

In one embodiment of the invention the heterologous immunoglobulin is an anti-Aβ antibody. In another embodiment the heavy chain variable domain of said anti-Aβ antibody comprises a CDR3 with an amino acid sequence selected from SEQ ID NO: 1, 2, or 3. In a further embodiment the light chain variable domain of said anti-Aβ antibody comprises a CDR3 with an amino acid sequence selected from SEQ ID NO: 4, 5, or 6. In a further embodiment said anti-Aβ antibody comprises a heavy chain variable domain with an amino acid sequence selected from SEQ ID NO: 7, 8, or 9. In still a further embodiment said anti-Aβ antibody comprises a light chain variable domain with an amino acid sequence selected from SEQ ID NO: 10, 11, or 12.

In one embodiment of the invention the heterologous immunoglobulin is an anti-P-Selectin antibody. In a further embodiment said anti-P-Selectin antibody comprises a heavy chain variable domain with an amino acid sequence selected from SEQ ID NO: 13, 14, or 15. In still a further embodiment said anti-P-Selectin antibody comprises a light chain variable domain with an amino acid sequence selected from SEQ ID NO: 16, 17, or 18.

In one embodiment of the invention the heterologous immunoglobulin is an anti-IL-13Rα antibody. In a further embodiment said anti-IL-13Rα antibody comprises a heavy chain variable domain with an amino acid sequence selected from SEQ ID NO: 19, 20, 21, 22, or 23. In still a further embodiment said anti-IL-13Rα antibody comprises a light chain variable domain with an amino acid sequence selected from SEQ ID NO: 24, 25, 26, 27, or 28.

In one embodiment of the invention the heterologous immunoglobulin is an anti-CD4 antibody-conjugate. In another embodiment the heavy chain variable domain of said anti-CD4 antibody in said conjugate comprises a CDR3 with an amino acid sequence selected from SEQ ID NO: 29, 30, or 31. In a further embodiment the light chain variable domain of said anti-CD4 antibody in said conjugate comprises a CDR3 with an amino acid sequence selected from SEQ ID NO: 32, 33, or 34. In a further embodiment said anti-CD4 antibody in said conjugate comprises a heavy chain variable domain with an amino acid sequence selected from SEQ ID NO: 35, 36, or 37. In still a further embodiment said anti-CD4 antibody in said conjugate comprises a light chain variable domain with an amino acid sequence selected from SEQ ID NO: 38, 39, or 40.

A mammalian cell usable for the large scale production of therapeutics, i.e. polypeptides intended for the use in humans, has to fulfill distinct criteria. Amongst others are these that it has to be cultivatable in serum-free, preferably in non-defined mammal-derived components free medium, or in a serum-free medium supplemented with defined mammal-derived components. Serum is a mixture of multitude of compounds. Normally bovine serum has been used for the cultivation of mammalian cells. With the arising problem of transmissible diseases from one species to another the use of serum and other non-defined mammal-derived compounds has to be avoided. The term "non-defined mammal-derived compound" as used within this application denotes compounds which are derived from a mammal, especially preferred from a cow, a pig, a sheep, or a lamb, and whose composition can be specified to less than 80%, preferably to less than 90% (w/w). A "defined mammal-derived compound" is a compound that is obtained from a mammal, especially preferred from a cow, a pig, a sheep, or a lamb, and whose composition can be specified to more than 95% (w/w), preferably to more than 98% (w/w), most preferably to more then 99% (w/w). An example of a defined mammal-derived compound is cholesterol from ovine wool, and galactose from bovine milk. In one embodiment the medium can be supplemented with defined or non-defined not mammal-derived compounds. An example of such a not mammal-derived compound is cod-liver oil.

Therefore in one embodiment of the current invention the medium used in the cultivation is a serum-free medium, or a serum-free medium supplemented with defined mammal-derived components, or an mammal-derived component free medium, or a protein-free medium, a protein-free medium supplemented with defined mammal-derived components, or a chemically defined medium, or a mammal-derived component free medium, or a defined protein-free medium. Examples of an mammal-derived component free medium are the CD CHO medium available from Invitrogen Corp., or the ProCHO4 available from Gibco. An example of a protein free medium is HyQ SFM4CHO available from Hyclone.

In another embodiment of the method according to the invention is the method beginning with the first transfection and ending with the recovery of the secreted heterologous immunoglobulin performed in the same medium. The term "in the same medium" denotes within the current application that beginning with the first transfection and ending with the recovery of the secreted heterologous immunoglobulin from the cultivation medium the same medium is used. This does not denote that the same additives have to be added to the medium in all steps, i.e. the medium may be supplemented with different additive in different steps of the method. Additives are compounds that are added to a medium in total to less than 20% (w/w), in one embodiment to less than 15% (w/w), in another embodiment to less than 10% (w/w). In one embodiment the medium used in the method according to the invention is the same medium in all steps and is a medium suitable for the large scale production of the secreted heterologous immunoglobulin.

It has surprisingly been found that with the method according to the invention a multiple transfected CHO cell can be obtained that has similar growth characteristics and an improved productivity compared to a one-time transfected CHO cell. The term "similar growth characteristics" denotes that the multiple transfected CHO cell grows to at least 50% of the cell density within the same time as the one-time transfected CHO cell. In another embodiment said multiple transfected CHO cell grows to at least 90% of the cell density as the one-time transfected cell. In still a further embodiment is the doubling time of the multiple transfected cell at most 150% of that of the one-time transfected cell. In one embodiment said multiple transfected CHO cell is a CHO cell transfected two or three times. In another embodiment the multiple transfected cell has an improved volumetric yield in a cultivation medium. The overall productivity of a large scale fermentation process is best determined by the volumetric yield, i.e. the amount of polypeptide per unit volume of the cultivation. This volumetric yield is the product of cell density, specific productivity of each cell and cultivation time. Thus, a cultivation with low cell density but high specific productivity will have the same volumetric yield in the same time as a cultivation with high cell density but low specific productivity in the same cultivation time. Thus, with the multiple transfected CHO cell and the method according to the invention a CHO cell is obtainable with similar growth characteristics but an improved volumetric yield/productivity compared to one-time transfected CHO cells.

The secreted heterologous immunoglobulin can be recovered from the cultivation medium with chromatographic methods known to a person of skill in the art. Therefore in one embodiment the method according to the invention comprises the final step of purifying said heterologous immunoglobulin with one or more chromatographic steps.

A vector suited for use in the method according to the invention comprises a prokaryotic origin of replication, and a first nucleic acid conferring resistance to a prokaryotic selection agent, and/or a second nucleic acid encoding the heavy chain of said heterologous immunoglobulin, and/or a third nucleic acid encoding the light chain of said heterologous immunoglobulin, and a fourth nucleic acid conferring resistance to a eukaryotic selection agent.

The comprised first nucleic acid confers resistance to the addition of a prokaryotic selection agent to the cultivation medium. Exemplary prokaryotic selection agents are e.g. ampicillin, kanamycin, chloramphenicol, tetracycline, or erythromycin. The term "a nucleic acid conferring resistance to a selection agent" and grammatical equivalents thereof denotes within the current application that the polypeptide encoded by said nucleic acid can neutralize said selection agent by modification or degradation or can counteract the effect of said selection agent. Thus, a cell comprising a nucleic acid conferring resistance to a selection agent has the ability to survive and proliferate with the selection agent present in the cultivation medium. Exemplary eukaryotic selection agents are e.g. neomycin, hygromycin, puromycin, methotrexate, Geneticin® (G418), or mycophenolic acid. The selection agent is chosen with the proviso that the prokaryotic and the eukaryotic selection agent is not a metal.

The transfection of the provided CHO cell according to the method according to the invention is performed as sequential steps of transfection and selection. CHO cells suitable in the method according to the invention are e.g. a CHO K1 cell, or a CHO DG44 cell, or a CHO XL99 cell, or a CHO DXB11 cell, or a CHO DP12 cell, or a super-CHO cell. Within the scope of the present invention, transfected cells may be obtained with substantially any kind of transfection method known in the art. For example, the nucleic acid may be introduced into the cells by means of electroporation or microinjection. Alternatively, lipofection reagents such as FuGENE 6 (Roche Diagnostics GmbH, Germany), X-tremeGENE (Roche Diagnostics GmbH, Germany), LipofectAmine (Invitrogen Corp., USA), and nucleotransfection (AMAX Corp.) may be used. Still alternatively, the nucleic acid may be introduced into the cell by appropriate viral vector systems based on retroviruses, lentiviruses, adenoviruses, or adeno-associated viruses (Singer, O., Proc. Natl. Acad. Sci. USA 101 (2004) 5313-5314).

After the transfection positive transfected cells are selected in the presence of selection agents, i.e. by selected growth. It has surprisingly been found that more than one eukaryotic selection agent can be present in the cultivation medium not interfering with growth and heterologous polypeptide expression if the cultivated CHO cell has been transfected with all required corresponding nucleic acids conferring resistance to these eukaryotic selection agents according to the current invention. It has also been found that CHO cells can be cultivated in the concomitant presence of three eukaryotic selection agents without a reduction of the doubling time to more than 150% of the doubling time of the non-transfected or one-time transfected CHO cell. Therefore, the multiple transfected CHO cell comprises nucleic acids, which are in each transfection step of the method according to the invention comprising a different, not previously transfected, nucleic acid as fourth nucleic acid which confers a new resistance not already present in said CHO cell to a different eukaryotic selection agent. Therefore, after the second transfection step a successfully transfected cell is selected for by cultivation in the concomitant presence of two different eukaryotic selection agents. After the third transfection the transfected cell can be cultivated for selection in the concomitant presence of three different eukaryotic selection agents.

Thus, the vector employed in the different transfection steps according to the method according to the invention is at least 95% identical on the nucleic acid level except for the nucleic acid conferring resistance to a eukaryotic selection agent, i.e. the fourth nucleic acid.

For the expression of a secreted heterologous immunoglobulin the vector with which the CHO cell is transfected and which comprises a nucleic acid conferring resistance to a eukaryotic selection agent also comprises a nucleic acid encoding the light chain of said heterologous immunoglobulin and/or a nucleic acid encoding the heavy chain of said heterologous immunoglobulin. If the vector comprises only a nucleic acid encoding either the light chain of said immunoglobulin or the heavy chain of said immunoglobulin said CHO cell is also transfected in each step by another vector comprising a nucleic acid encoding the corresponding other chain of said immunoglobulin.

In one embodiment the first to fourth nucleic acid sequence comprised in the transfection vectors according to the invention (i.e. the first, second, and third transfection vector) is contained in an expression cassette. An "expression cassette" refers to a construct that contains the necessary regulatory elements, such as promoter and polyadenylation site, for expression of at least the contained nucleic acid in a cell, e.g. a promoter, a nucleic acid to be expressed, and a transcription terminator including a polyadenylation signal. The promoter contained in the expression cassette determines the amount of transcription of the operably linked nucleic acid and therewith it determines the amount of the translation of said nucleic acid. A first promoter inducing a larger amount of translation of a nucleic acid compared to a second promoter is termed a "stronger promoter" with respect to said second promoter. It is intended to produce the secreted heterologous immunoglobulin and not the polypeptide conferring resistance to a selection agent. Thus, the capacity of the host cells transcription and translation machinery has to be split up correspondingly. Therefore, in one embodiment the promoter employed for the transcription of said second and third nucleic acids is different from the promoter employed for the transcription of said fourth nucleic acid. In another embodiment is the amount of transcript of said second and third nucleic acid encoding the chains of said heterologous immunoglobulin larger than the amount of transcript of said forth nucleic acid conferring resistance to a selection agent. Thus, the promoter employed for the expression of said second and third nucleic acid is stronger than the promoter employed for the expression of said fourth nucleic acid. In another embodiment is the promoter employed for the transcription of said second and third nucleic acids the same but different from the promoter of said fourth nucleic acid. In one embodiment the promoter for the expression of said second and third nucleic acid is the CMV promoter or a variant thereof and the promoter for the expression of said fourth nucleic acid is the SV40 promoter or a variant thereof.

In a further embodiment of the method according to the invention the codon usage of said second and third nucleic acid is optimized for the expression in CHO cells. This allows a more efficient use of the transfer-RNAs present in the recombinant CHO cell. In another embodiment said second and/or third nucleic acid comprise an intronic nucleic acid sequence, in another embodiment the intronic nucleic acid is a mouse/human hybrid intron. In the genome of eukaryotic cells the genomic DNA sequences contain coding (exonic) and non-coding (intronic) nucleic acid sequences. After transcription of the DNA to the pre-mRNA, the pre-mRNA also contains these intronic and exonic nucleic acid sequences. Prior to translation the non-coding intronic nucleic acid sequences are removed during mRNA processing by splicing them out of the primary mRNA transcript to generate the mature mRNA. The splicing of the primary mRNA is controlled by a splice donor site in combination with a properly spaced apart splice acceptor site. The splice donor site is located at the 5' end and the splice acceptor site is located at the 3' end of an intronic sequence and both are only partly removed during the pre-mRNA splicing.

To produce a secreted polypeptide, the nucleic acid(s) encoding the chains of the heterologous immunoglobulin include a DNA segment that encodes a signal sequence/leader peptide. The signal sequence directs the newly synthesized polypeptide to and through the Endoplasmatic reticulum (ER) membrane where the polypeptide can be routed for secretion. The signal sequence is cleaved off by a signal peptidases during crossing of the ER membrane. As for the function of the signal sequence the recognition by the host cell's secretion machinery is essential. Therefore, the used signal sequence has to be recognized by the host cell's proteins and enzymes of the secretion machinery.

In one embodiment the method according to the invention comprises a third transfection step in step c):
  (v) transfecting said CHO cell selected in (iv) with said vector comprising a fourth nucleic acid sequence different from that in the transfection vector used in (i) and (iii) conferring resistance to a third eukaryotic selection agent, which is different from said first and said second eukaryotic selection agent,
  (vi) selecting a CHO cell transfected in (v) by selected growth in a cultivation medium containing said first and said second and said third eukaryotic selection agent.

In this embodiment the cultivation medium employed for the cultivation of said transfected CHO cell in step d) further comprises a third eukaryotic selection agent.

A second aspect of the current invention is a CHO cell expressing a secreted heterologous immunoglobulin obtainable with the following method:
a) providing a CHO cell, which is
  adapted to growth in suspension culture,
  adapted to growth in serum-free medium,
  mycoplasma free,
b) providing a nucleic acid comprising
  a prokaryotic origin of replication,
  a first nucleic acid sequence conferring resistance to a prokaryotic selection agent,
  a second nucleic acid sequence encoding the heavy chain of said heterologous immunoglobulin, and a third nucleic acid sequence encoding the light chain of said heterologous immunoglobulin,
  whereby a first transfection vector is provided which comprises said provided nucleic acid and an additional fourth nucleic acid sequence conferring resistance to a first eukaryotic selection agent,
  whereby a second transfection vector is provided which comprises said provided nucleic acid and an additional fourth nucleic acid sequence different from the fourth nucleic acid in said first transfection vector conferring resistance to a second eukaryotic selection agent, whereby said second eukaryotic selection agent is different to said first eukaryotic selection agent,
c) transfecting and selecting said CHO cell, wherein said transfecting and selecting comprises the following steps in the following order:
  (i) transfecting said CHO cell with said first transfection vector,
  (ii) selecting a CHO cell transfected in (i) by selected growth in a cultivation medium containing a first eukaryotic selection agent to which the first transfection vector confers resistance, (iii) transfecting said CHO cell selected in (ii) with said second transfection vector, (iv) selecting a CHO cell transfected in (iii) by selected growth in a cultivation medium containing said first eukaryotic selection agent, to which the first transfection vector confers resistance, and said second eukaryotic selection agent, to which the second transfection vector confers resistance.

The term "virus free" which is used within this application denotes that the CHO cell does not contain any viral nucleic acid which would result if expressed during cultivation in harmful, in down stream processing operations not separatable products for humans.

The following examples, and figures are provided to aid the understanding of the present invention, the true scope of which is set forth in the appended claims. It is understood that modifications can be made in the procedures set forth without departing from the spirit of the invention.

(B) Specific production rates of clones obtained after subcloning with limited dilution and of clones obtained with the method according to the invention; X-axis: (1) G24, (2) limited dilution, (3) method according to the invention; Y-axis: specific production rate [pg/d*cell].

Figure 7:
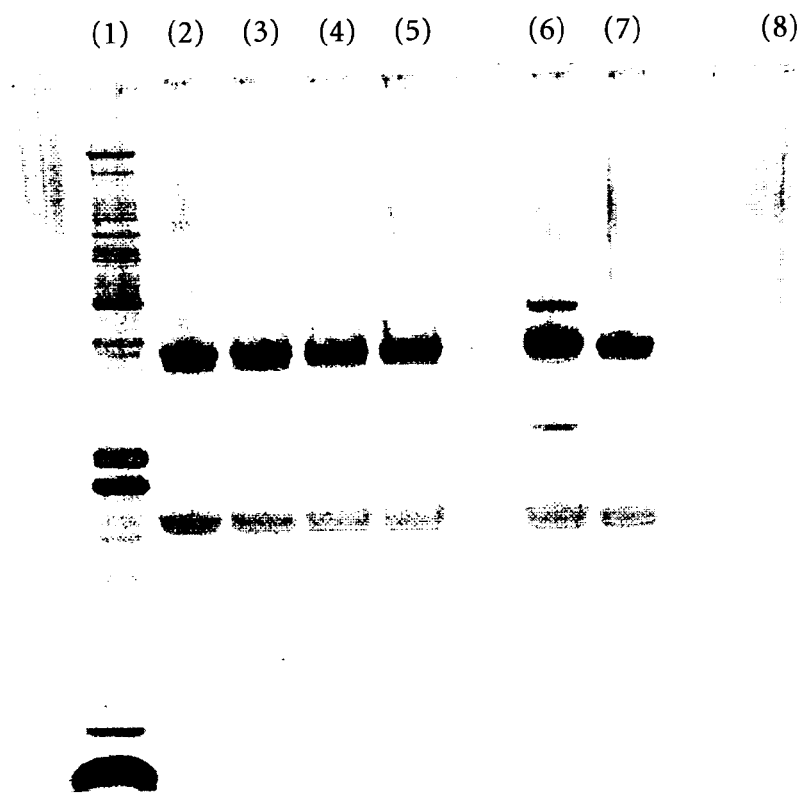

FIG. 7 SDS-Page after protein-A HPLC purification of the antibody. For the four samples 35-45, 37-65, 39-4 and 43-16 two bands are visible, the upper being the heavy chain, the lower being the light chain. Sample 25g7 is a control antibody with antibody-related side products (above the heavy chain and between heavy and light chain). Samples: (1) Molecular weight marker, (2) 35-45, (3) 37-65, (4) 39-4, (5) 43-16, (6) 25g7, (7) Reference antibody, (8) Medium 25×.

Figure 8:
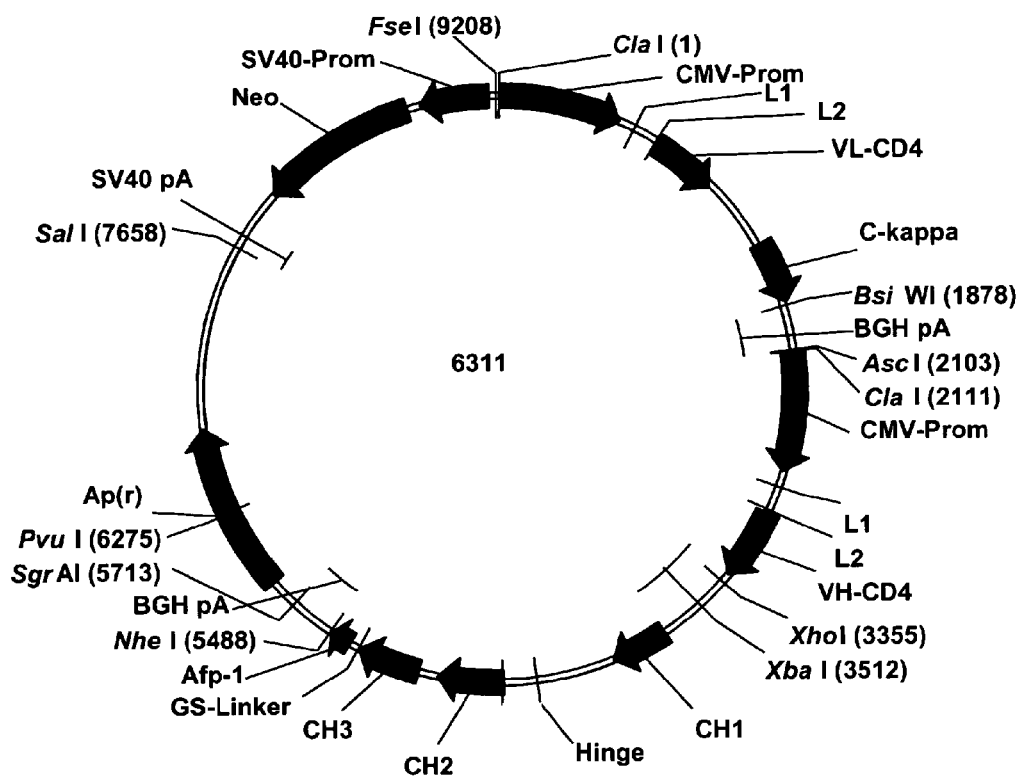
Figure 9:
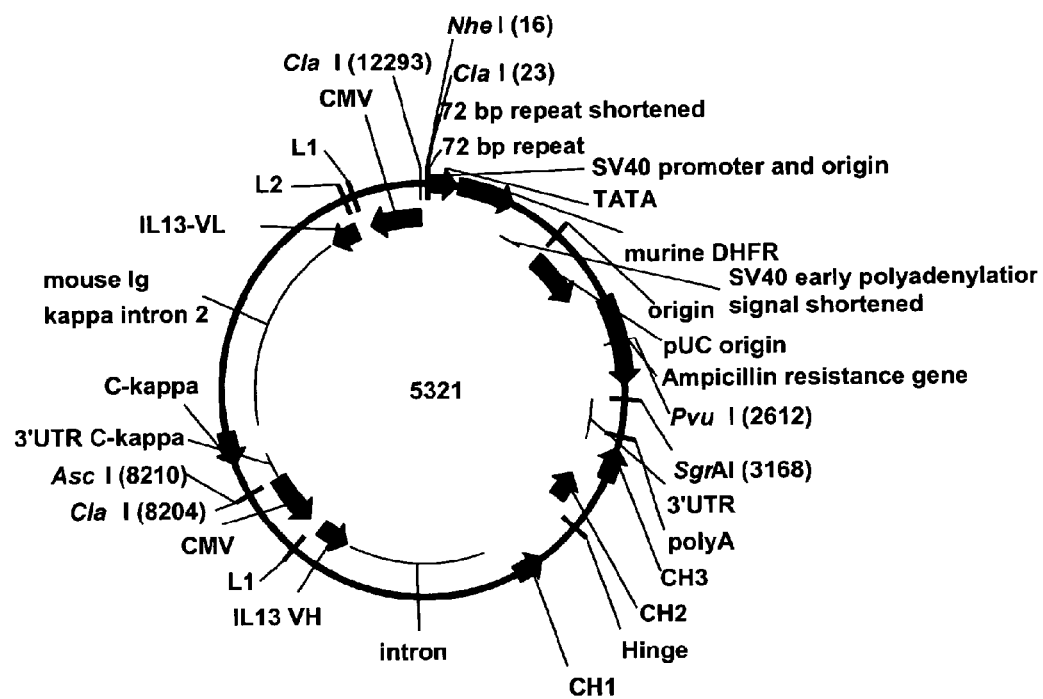

FIG. 8 Annotated plasmid map of plasmid p6311.
FIG. 9 Annotated plasmid map of plasmid p5321.

EXAMPLES

Materials & Methods

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, Md. (1991). Amino acids of antibody chains are numbered according to EU numbering (Edelman, G. M., et al., Proc. Natl. Acad. Sci. USA 63 (1969) 78-85; Kabat, E. A., et al., Sequences of Proteins of Immunological Interest, 5th ed., Public Health Service, National Institutes of Health, Bethesda, Md., (1991)).

Recombinant DNA Techniques:

Standard methods were used to manipulate DNA as described in Sambrook, J., et al., Molecular cloning: A laboratory manual; Cold Spring Harbor Laboratory Press, Cold Spring Harbor, N.Y., 1989. The molecular biological reagents were used according to the manufacturer's instructions.

Gene Synthesis:

Desired gene segments were prepared from oligonucleotides made by chemical synthesis. The 100-600 bp long gene segments, which are flanked by singular restriction endonuclease cleavage sites, were assembled by annealing and ligation of oligonucleotides including PCR amplification and subsequently cloned into the pCR2.1-TOPO-TA cloning vector (Invitrogen Corp., USA) via A-overhangs or pPCR-Script Amp SK(+) cloning vector (Stratagene Corp., USA). The DNA sequence of the subcloned gene fragments were confirmed by DNA sequencing.

Protein Determination:

Protein concentration was determined by determining the optical density (OD) at 280 nm, using the molar extinction coefficient calculated on the basis of the amino acid sequence.

Antibody Titer Determination:

Antibody titers were determined either by anti-human Fc ELISA or by Protein A chromatography using the autologous purified antibody as a reference.

SDS-PAGE

LDS sample buffer, fourfold concentrate (4×): 4 g glycerol, 0.682 g TRIS-Base, 0.666 g TRIS-hydrochloride, 0.8 g LDS (lithium dodecyl sulfate), 0.006 g EDTA (ethylene diamin tetra acid), 0.75 ml of a 1% by weight (w/w) solution of Serva Blue G250 in water, 0.75 ml of a 1% by weight (w/w) solution of phenol red, add water to make a total volume of 10 ml.

The culture broth containing the secreted antibody was centrifuged to remove cells and cell debris. An aliquot of the clarified supernatant was admixed with ¼ volumes (v/v) of 4xLDS sample buffer and ¹⁄₁₀ volume (v/v) of 0.5 M 1,4-dithiothreitol (DTT). Then the samples were incubated for 10 min. at 70° C. and protein separated by SDS-PAGE. The NuPAGE® Pre-Cast gel system (Invitrogen Corp.) was used according to the manufacturer's instruction. In particular, 10% NuPAGE® Novex® Bis-TRIS Pre-Cast gels (pH 6.4) and a NuPAGE® MOPS running buffer was used.

Western Blot

Transfer buffer: 39 mM glycine, 48 mM TRIS-hydrochloride, 0.04% by weight (w/w) SDS, and 20% by volume methanol (v/v)

After SDS-PAGE the separated antibody chains were transferred electrophoretically to a nitrocellulose filter membrane (pore size: 0.45 µm) according to the "Semidry-Blotting-Method" of Burnette (Burnette, W. N., Anal. Biochem. 112 (1981) 195-203).

Example 1

Expression Vector for Expressing an Anti-Aβ Antibody

An example (preferably monoclonal) antibody for which a cell line for expression can be obtained according to the current invention is an antibody against the amyloid β-A4 peptide (anti-Aβ antibody). Such an antibody and the corresponding nucleic acid sequences are, for example, reported in WO 2003/070760 or US 2005/0169925 or in SEQ ID NO: 1 to 12.

The anti-Aβ antibody expressing Chinese hamster ovary (CHO) cell line was generated by three successive complete transfections and selection campaigns.

A genomic human κ-light chain constant region gene segment (C-kappa, $C_L$) was added to the light chain variable region of the anti-Aβ antibody, while a human γ1-heavy chain constant region gene segment ($C_{H1}$-Hinge-$C_{H2}$-$C_{H3}$) was added to the heavy chain variable region of the anti-Aβ antibody. The complete κ-light and γ1-heavy chain antibody genes were then joined with a human cytomegalovirus (HCMV) promoter at the 5'-end and a human immunoglobulin polyadenylation signal sequence at the 3'-end.

a) Heavy Chain Expression Cassette

The transcription unit of the anti-Aβ antibody heavy chain is composed of the following elements:

- the immediate early enhancer and promoter from the human cytomegalovirus,
- a 5'-untranslated region derived from a human antibody germline gene,
- the anti-Aβ antibody heavy chain variable domain including a signal sequence derived from a human antibody germline gene,
- a human/mouse heavy chain hybrid intron 2 including the mouse Ig heavy chain enhancer element (see e.g. (Neuberger, M. S., EMBO J. 2 (1983) 1373-1378),
- the genomic human γ1-heavy chain gene constant region,
- the human immunoglobulin γ1-heavy chain polyadenylation ("poly A") signal sequence,
- the unique restriction sites AscI and SgrAI at the 5'- and 3'-end, respectively.

b) Light Chain Expression Cassette

The transcription unit of the anti-Aβ antibody light chain is composed of the following elements:

- the immediate early enhancer and promoter from the human cytomegalovirus (HCMV),
- a 5'-untranslated region derived from a human antibody germline gene,
- the anti-Aβ antibody light chain variable region including a signal sequence derived from a human antibody germline gene,
- a human/mouse κ-light gene hybrid intron 2 including the mouse Ig χ-light chain enhancer element (Picard and Schaffner, A lymphocyte-specific enhancer in the mouse immunoglobulin kappa gene. Nature 307 (1984) 80-82),
- the human κ-light gene constant region (C-kappa),
- the human immunoglobulin κ-polyadenylation ("poly A") signal sequence,
- the unique restriction sites Sse8387 and FseI at the 5'- and 3'-end, respectively.

c) Expression Plasmids 5128, 5137, and 5151

For expression and production of the anti-Aβ antibody the light and heavy chain expression cassettes were placed on a single expression vector (heavy chain upstream of light chain in clockwise orientation). Three identical expression vectors were generated differing only in the selectable marker gene included, in particular, in the gene conferring resistance to the selection agent neomycin, hygromycin, or puromycin. The vectors also include a mouse DHFR gene which was not used for selection or amplification.

The expression vectors contain beside the light and heavy chain expression cassette the following elements:

- a selectable marker (either a neomycin, hygromycin or puromycin resistance gene),
- an origin of replication allowing for the replication of the plasmid in *E. coli*,
- a beta-lactamase gene which confers ampicillin resistance in *E. coli*,
- a mouse derived DHFR gene.

Figure 1:
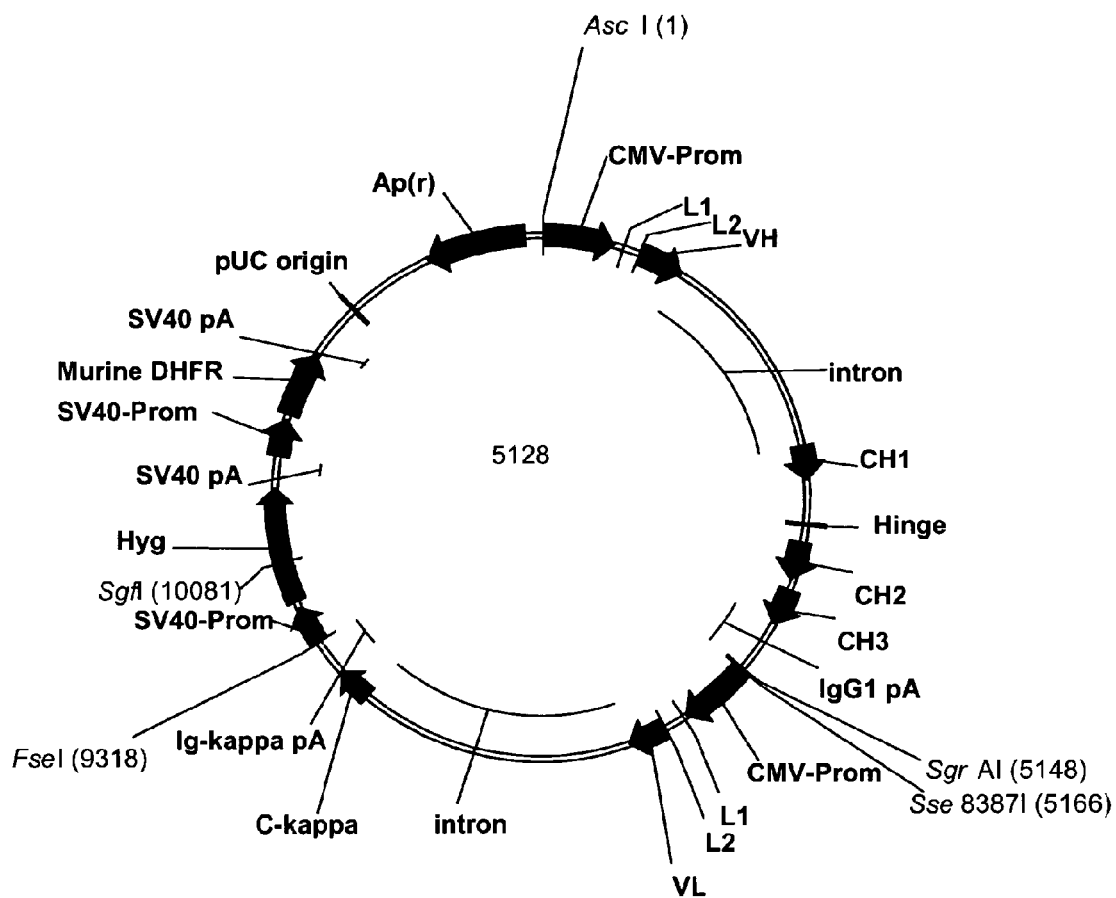
FIG. 1 Annotated plasmid map of plasmid p5128.
Figure 2:
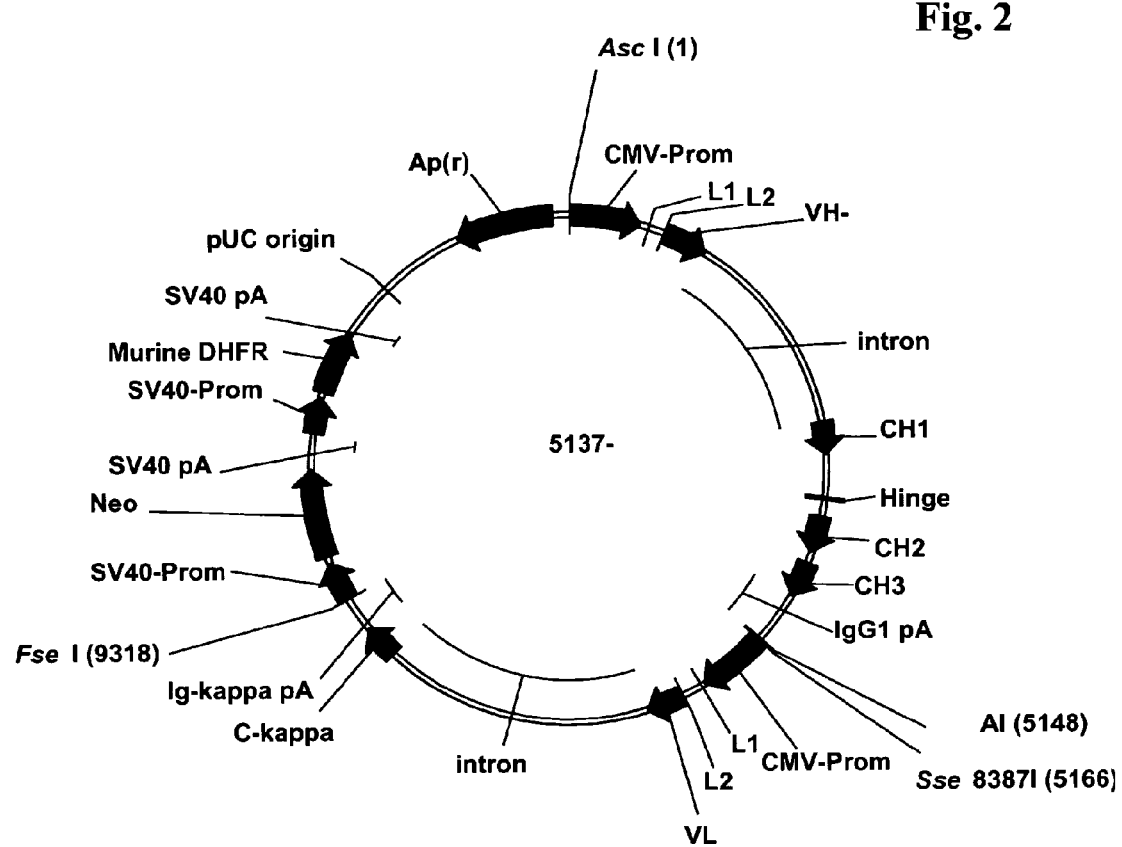
FIG. 2 Annotated plasmid map of plasmid p5137.
Figure 3:
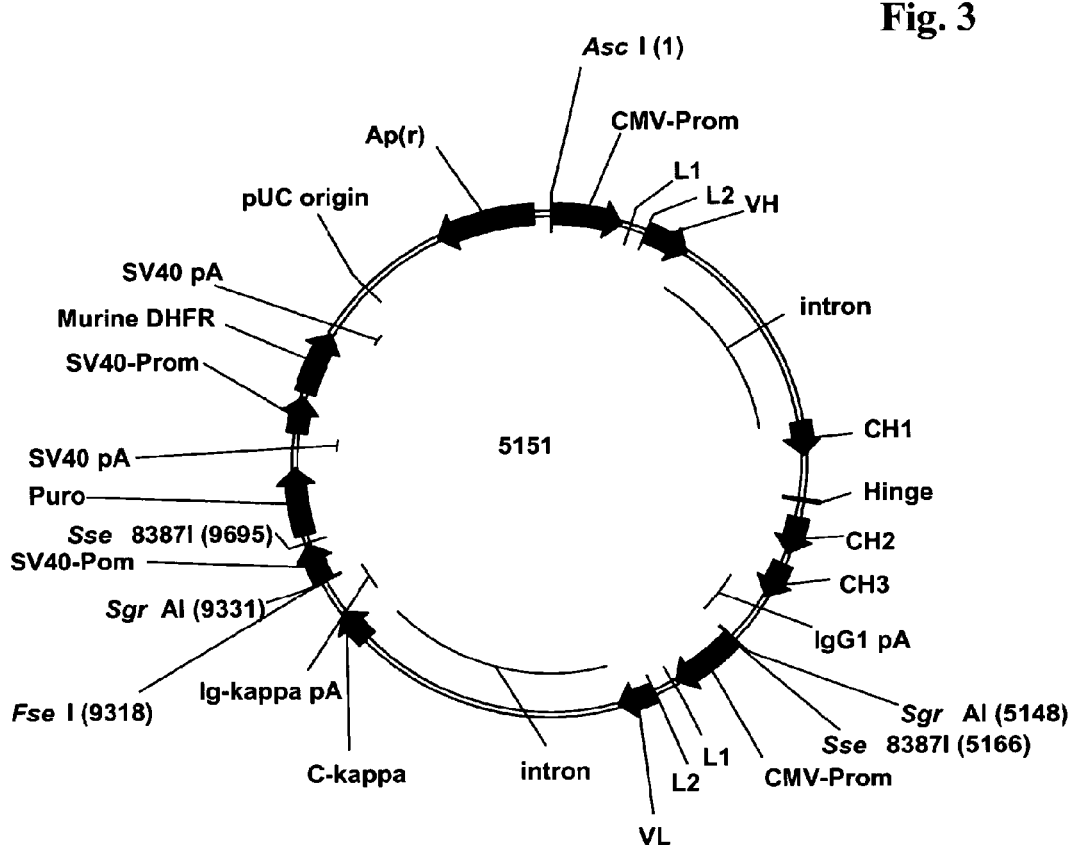
FIG. 3 Annotated plasmid map of plasmid p5151.

The plasmid map of the expression vector 5128 containing a hygromycin selectable marker gene is shown in FIG. 1. The plasmid map of the expression vector 5137 containing a neomycin selectable marker gene is shown in FIG. 2. The plasmid map of the expression vector 5151 containing a puromycin selectable marker gene is shown in FIG. 3.

Example 2

Transfection and Selection of a CHO Cell Expressing an Anti-Aβ Antibody

Parent CHO-K1 cells, pre-adapted to growth in serum-free suspension culture in synthetic animal component free ProCHO4 medium (Cambrex Corp.) containing 8 mM glutamine and 1×HT supplement (Gibco/Invitrogen) were used as host cell line. This supplemented ProCHO4 medium is designated in the following as ProCHO4-complete medium. The adherent growing CHO-K1 parent cell line was received from ATTC as ATCC CCL-61.

The preadapted parent host cells were propagated in suspension in synthetic, animal component-free ProCHO4-complete medium under standard humidified conditions (95%, 37° C., and 5% $CO_2$). On regular intervals depending on the cell density the cells were splitted into fresh medium. The cells were harvested by centrifugation in the exponential growth phase, washed once in sterile Phosphate Buffered Saline (PBS) and resuspended in sterile PBS.

Prior to transfection the anti-Aβ antibody expressing plasmids were linearized within the β-lactamase gene (*E. coli* ampicillin resistance marker gene) using the restriction endonuclease enzyme PvuI or AviII. The cleaved DNA was precipitated with ethanol, dried under vacuum, and dissolved in sterile PBS.

In general, for transfection, the (parent or already transfected) CHO cells were electroporated with 20-50 μg linearized plasmid DNA per approximately $10^7$ cells in PBS at room temperature. The electroporations were performed with a Gene Pulser XCell electroporation device (Bio-Rad Laboratories) in a 2 mm gap cuvette, using a square wave protocol with a single 180 V pulse. After transfection, the cells were plated out in ProCHO4-complete medium in 96-well culture plates. After 24 h of growth a solution containing one or more selection agents were added (ProCHO4-complete selection medium; G418: 400 μg/ml; hygromycin: 600 μg/ml; puromycin: 8 μg/ml). Once a week the ProCHO4-complete selection medium was replaced. The antibody concentration of the anti-Aβ antibody was analyzed with an ELISA assay specific for human IgG1 in the culture supernatants.

For selection of high-yield anti-Aβ antibody production cell lines the productivity was tested in ProCHO4-complete selection medium after propagation in 6-well culture plates, T-flasks and/or Erlenmeyer shake flasks using an anti-human IgG1 ELISA and/or analytic Protein A HPLC.

Subclones were obtained by two methods, Limiting Dilution (LD) and Fluorescence Activated Cell Sorting (FACS).

Limiting Dilution:

For limiting dilution cells were plated out in ProCHO4-conditioned medium (consisting of 50% (v/v) fresh ProCHO4-complete selection medium and 50% (v/v) ProCHO4-complete conditioned selection medium derived from the cells to be propagated) at a cell density of 0.5-2 cells per 0.1 ml medium per well of a 96-well culture plate. Once a week the medium was replaced by ProCHO4-complete selection medium. The antibody concentration of the anti-Aβ antibody was analyzed by an ELISA assay specific for human IgG1 in the culture supernatants.

Single Cell Deposition by Flow Cytometry Including Identification and Isolation of Clones:

The identification and isolation of stably transfected clones was performed with the aid of a cell surface labeling technique using fluorescently tagged Protein A that binds to secreted but still membrane-attached antibodies. The fluorescence intensity of the stained cells was used as criterion for cell selection.

In the case of fluorescence activated cell sorting the electroporated population of cells were directly seeded into T-flasks in ProCHO4-complete medium. The appropriate selection agent or agents (G418, hygromycin, and/or puromycin) was/were added to the culture one day after transfection and the transfectant pool was expanded.

Cells from the expanded transfectant pool were first treated with Accumax (PAA Laboratories) for 15 minutes at 37° C. and then passed through a 40 µM nylon mesh to remove remaining large cell aggregates. The cells were collected by centrifugation, resuspended in PBS containing 5% FCS (Gibco/Invitrogen) at a cell density of $10^6$ to $10^7$ cells/ml and incubated for 20 minutes on ice. Thereafter, the cells were stained with 10 ng/ml Protein A Alexa Fluor 488 (Molecular Probes Inc.) in a volume of 8 ml FCS-PBS for 30 minutes on ice in the dark. Afterwards, the cells were washed once with 5% FCS-PBS and once with ProCHO4 medium containing 8 mM Ultra Glutamine (Cambrex Corp.), 1×HT supplement and 5% FCS. Finally the cells were resuspended in the supplemented ProCHO medium used for washing at a cell density of $10^6$ to $10^7$ cells/ml and transferred to a BD FACSAria cell sorter (BD Biosciences).

Single cells were sorted by flow cytometry and deposited in wells of 96-well culture plates containing of ProCHO4-conditioned medium. The selected and deposited cells encompassed cells with the top 10%, 7%, or 4% of fluorescence intensity of the gated live cells. After 48 hours ProCHO4 complete selection medium containing the appropriate selection agent in 2-fold concentration was added to each well. Once a week the medium was replaced with ProCHO4-complete selection medium. The antibody concentration of the anti-Aβ antibody was analyzed with an ELISA assay specific for human IgG1 in the culture supernatants.

Transfection and Selection Steps:

For the first transfection and selection step the plasmid 5137 has been used. Plasmid 5137 has been transfected with electroporation into parent cell line adapted to growth in ProCHO4-complete medium. The transfected cells were cultivated in ProCHO4-complete medium supplemented with up to 700 µg/ml G418 in 96 well plates. The antibody concentration in the culture supernatants was evaluated by an anti-human IgG1 ELISA. Approximately 1000 clones have been tested and the selected of them were further cultivated in 24-well plates, 6-well plates and subsequently in shaker flasks. The growth and productivity of approximately 20 clones was assessed in static and suspension cultures by anti-human IgG1 ELISA and/or analytic protein A HPLC. The best clone (best clone does not denote the most productive clone it denotes the clone with the best properties for the further steps) was subcloned by limited dilution in ProCHO4-conditioned medium supplemented with 700 µg/ml G418. The selected clone was named 8C8.

For the second transfection and selection step the plasmid 5128 has been used. Plasmid 5128 has been transfected with electroporation into cell line clone 8C8 cultivated in ProCHO4-complete medium supplemented with 700 µg/ml G418. The transfected cells were expanded for about two to three weeks in ProCHO4-conditioned medium supplemented with 200 µg/ml G418 and 300 µg/ml hygromycin (ProCHO4-double selection medium). Single antibody secreting cells were identified and deposited on the basis of their fluorescence intensity after staining with a Protein A Alexa Fluor conjugate by FACS analysis. The deposited cells were cultivated in ProCHO4-double selection medium in 96 well plates. The antibody concentration in the culture supernatants was evaluated by an anti-human IgG1 ELISA. Approximately 500 clones have been tested and the selected of them were further cultivated in 24-well plates, 6-well plates and subsequently in shaker flasks. The growth and productivity of approximately 14 clones was assessed in static and suspension cultures by anti-human IgG1 ELISA and/or analytic Protein A HPLC. The selected clone was named 4F5.

For the third transfection and selection step the plasmid 5151 has been used. Plasmid 5151 has been transfected with electroporation into cell line clone 4F5 cultivated in ProCHO4-double selection medium. The transfected cells were expanded for about two to three weeks in ProCHO4-triple selection medium (ProCHO4-conditioned medium supplemented with 200 µg/ml G418 and 300 µg/ml hygromycin and 4 µg/ml puromycin). Single antibody secreting cells were identified and deposited on the basis of their fluorescence intensity after staining with a Protein A Alexa Fluor conjugate by FACS analysis. The deposited cells were cultivated in ProCHO4-triple selection medium in 96 well plates. The antibody concentration in the culture supernatants was evaluated by an anti-human IgG1 ELISA. Approximately 500 clones have been tested and the selected of them were further cultivated in 24-well plates, 6-well plates and subsequently in shaker flasks. The growth and productivity of approximately 10 clones was assessed in static and suspension cultures by anti-human IgG1 ELISA and/or analytic protein A HPLC. The selected clone was named 20F2.

Clone 20F2 has been selected based on his growth, productivity, and product quality characteristics after growth in fed-batch suspension culture in ProCHO4-triple selection medium, i.e. in the concomitant presence of the three selecting agents G418, hygromycin, and puromycin.

Clone Characteristics:

As can be seen from the following table the doubling time and cell density after three days of cultivation were comparable when the basic cell line CHO-K1 (wild-type) and the selected clones are compared.

TABLE 1

Growth characteristics

| Clone | Doubling time [h] | Starting cell density [$10^6$ cells/ml] | Cell density at day 3 [$10^6$ cells/ml] | Viability at day 3 [%] |
|---|---|---|---|---|
| CHO-K1 (wild-type) | 22-23 | 3 | 18-20 | 97-98 |
| 8C8 | 26-28 | 3 | 12-15 | 96-98 |
| 4F5 | 22-24 | 3 | 24-27 | 96-97 |
| 20F2 | 24-26 | 2 | 23-26 | 97-98 |

Example 3

Stability of Clone 20F2 Expressing an Anti-Aβ Antibody

Stability of growth and product formation was evaluated in sequential cell subculture over a time period of 60 days (about 60 generations) in the presence and absence of the selection agents (with and without antibiotics). The cultivation was performed as described above.

TABLE 2

Characteristics of clone 20F2.

| Parameter | Clone 20F2 | |
|---|---|---|
| | cultivation in the presence of three selection agents | cultivation in the absence of selection agents |
| Mean value viability [%] | 97 | 97 |
| Mean value doubling time [h] | 27 | 26 |
| Mean value SPR [pg/c/d] | 11 | 9 |

Following extensive passage (up to generation 60) no evidence was obtained indicating that the anti-Aβ antibody producing clone 20F2 was unstable with respect to cell growth and product formation in the presence or absence of the three selection agents, respectively.

Example 4

Expression Vector for Expressing an Anti-P-Selectin Antibody

Another example (preferably monoclonal) antibody for which a cell line for expression can be obtained according to the current invention is an antibody against the human P-Selectin glycoprotein (anti-P-Selectin antibody). Such an antibody and the corresponding nucleic acid sequences are for example described in WO 2005/100402, or US 2005/0226876 or SEQ ID NO: 13 to 18.

The anti-P-Selectin antibody expressing Chinese hamster ovary cell line was generated by two successive complete transfections and clone selection campaigns.

A genomic human kappa-light chain constant region gene segment (C-kappa) was added to the light chain variable region of the anti-P-Selectin antibody, whereas a human gamma 4-heavy chain constant region gene segment ($C_{H1}$-Hinge-$C_{H2}$-$C_{H3}$) was added to the heavy chain variable region of the anti-P-Selectin antibody. The complete kappa-light and gamma 4-heavy chain antibody genes were then joined with a human cytomegalovirus immediate early promoter and enhancer (CMV IE) at the 5'-end and the Simian Virus 40 early polyadenylation (SV 40 early poly A) signal sequence at the 3'-end.

a) Heavy Chain Expression Cassette

The transcription unit of the anti-P-Selectin antibody heavy chain is composed of the following elements:
- the immediate early enhancer and promoter from the human cytomegalovirus (CMV IE),
- a 5'-untranslated region (5' UTR),
- the coding sequence for the anti-P-Selectin antibody gamma 4-heavy chain including a signal peptide in an intron-exon gene structure,
- the SV 40 early poly A signal sequence.

b) Light Chain Expression Cassette

The transcription unit of the anti-P-Selectin antibody light chain is composed of the following elements:
- the immediate early enhancer and promoter from the human cytomegalovirus (CMV IE),
- a 5'-untranslated region (5' UTR),
- the coding sequence for the anti-P-Selectin kappa-light chain in an intron-exon gene structure,
- the SV 40 early poly A signal sequence.

c) Expression Plasmids 5057 and 5069

For the expression and production of the anti-P-Selectin antibody the light and heavy chain expression cassettes were placed on a single expression vector (light chain upstream of heavy chain). Two identical expression vectors were generated differing only in the selectable marker gene included, in particular, the murine dihydrofolate reductase (DHFR) gene or a neomycin resistance gene.

The expression vectors contain beside the light and heavy chain expression cassette the following elements:
- a selectable marker, either the murine DHFR gene or a gene conferring resistance to the selection agent neomycin under the control of the SV40 early promoter and origin,
- an origin of replication allowing for the replication of the plasmid in E. coli taken from pUC19 (pUC origin),
- a beta-lactamase gene which confers ampicillin resistance in E. coli.

Figure 4:
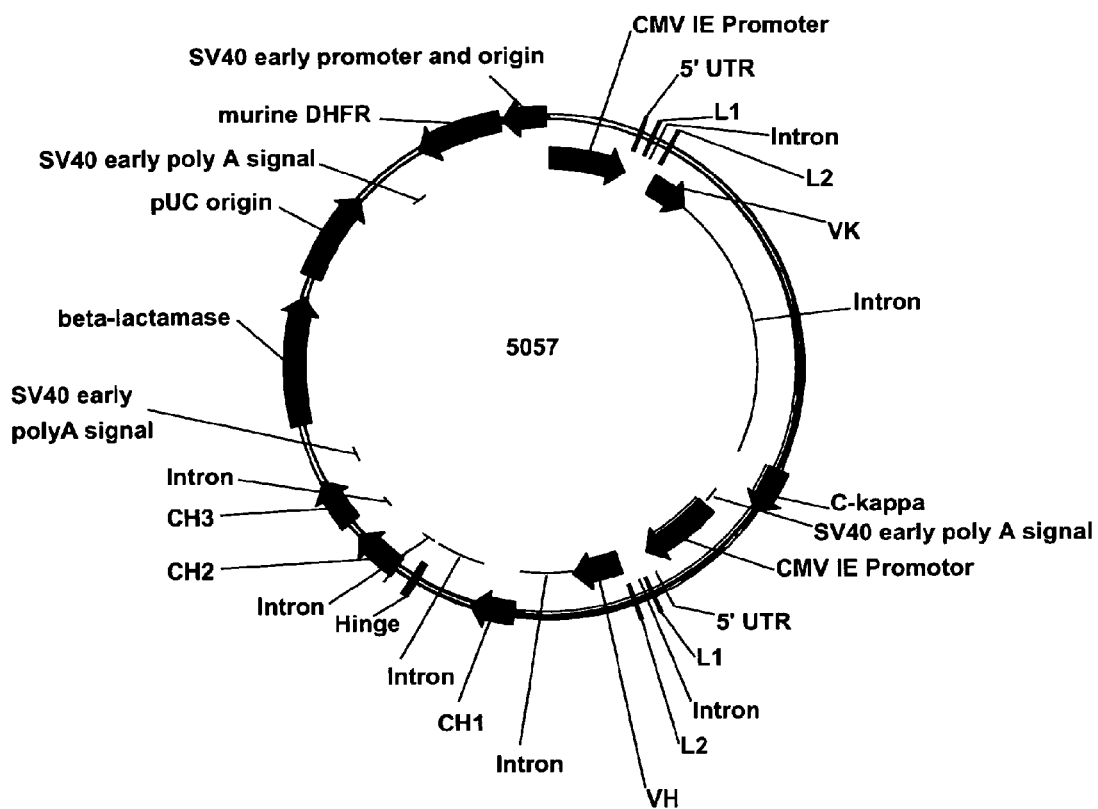
FIG. 4 Annotated plasmid map of plasmid p5057.
Figure 5:
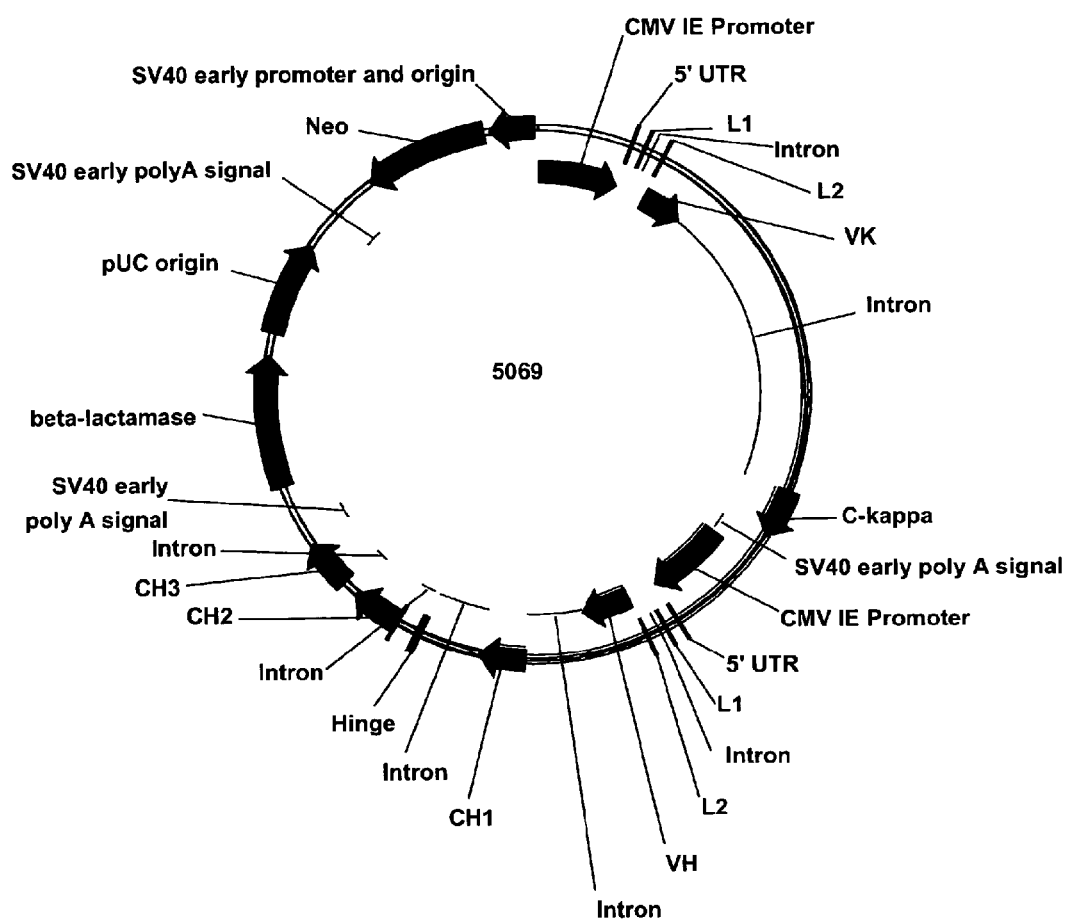
FIG. 5 Annotated plasmid map of plasmid p5069.

The plasmid map of the expression vector 5057 containing the murine DHFR marker gene is shown in FIG. 4. The plasmid map of the expression vector 5069 containing a neomycin selectable marker gene is shown in FIG. 5.

Example 5

Transfection and Selection of a CHO Cell Line Expressing an Anti-P-Selectin Antibody CHO-K1 cells, pre-adapted to growth in serum-free suspension culture in protein-free HyQ SFM4CHO medium (Hyclone, Cat. No. SH30549) supplemented with defined animal-derived components (cholesterol from ovine wool and cod-liver oil) were used as the host cell line. The cells were propagated in shake flasks in protein-free HyQ SFM4CHO medium under standard humidified conditions (95%, 37° C., and 5% $CO_2$) and under constant agitation at 150 rpm/min. Depending on the cell density the cells were split into fresh medium.

The adherent CHO-K1 cell lines had been obtained from the American Type Culture Collection as ATCC CCL-61.

First Transfection and Selection

Prior to transfection the expression plasmid 5057 was linearized within the beta-lactamase gene using the restriction enzyme PvuI. The cleaved DNA was purified using QiaQuick spin columns (Qiagen) according to the manufacturer's recommendations.

Transfection was carried out by electroporation using Gene Pulser XCell (BIO-RAD) and 0.2 cm-cuvettes (BIO-RAD, Cat. No. 165-2086). For transfection $10^6$ to $10^7$ CHO-K1 cells were harvested by centrifugation, resuspended in PBS, transferred to the cuvette and mixed with 20-50 μg linearized plasmid DNA. The cells were exposed to a single square wave pulse (160 V, 15 ms) and subsequently diluted in HyQ SFM4CHO medium to a density of approx. $4 \times 10^5$ cells/ml and seeded in a T75 cell culture flask. After 48 hours of propagation without the supplementation of a selection agent, the cells were diluted in HyQ SFM4CHO medium supplemented with 200 nM MTX to a density of $10^4$ to $10^5$ cells/ml and seeded in 96-well plates with 3-7000 cells per well. After approx. two weeks, fresh medium was added per well and after additional two weeks the culture medium was completely replaced by fresh medium. Four days later the culture supernatants were tested for antibody production by anti-human Fc ELISA. In total approximately 600 clones were screened.

45 clones with antibody titers of more than 10 μg/ml were picked and transferred to 48-well plates. The clones were expanded to shaker flasks over additional passages and subsequently transferred to serum free production medium for the final productivity assessment. A 125 ml shaker flask was inoculated with $10^5$ to $10^6$ cells/ml in medium supplemented with 200 nM MTX. Viable cell density and viability were monitored over one week. Antibody titers were measured by Protein A chromatography on the final day. Based on these data, clone G24 was selected for further development. G24 reached a maximal viable cell density of 3.3×10⁶ cells/ml. The antibody titer was 402 µg/ml. The average specific production rate (SPR) was 28 pg/(cell*d).

Second Transfection and Selection:

Clone G24 was subjected to a second transfection. For the second transfection plasmid 5069 was used. Linearization and purification of the plasmid as well as electroporation of G24 were performed as described for the first transfection. After 48 hours of propagation without selection pressure, the cells were diluted in HyQ SFM4CHO medium supplemented with 200 nM MTX and 400 µg/ml G418 to a density of 10³ to 10⁴ cells/ml and seeded in 96-well plates with 500 cells per well. After approx. two weeks, fresh medium was added per well and after an additional week the culture medium was completely replaced by fresh medium. Four days later the culture supernatants were tested for antibody production by anti-human Fc ELISA. In total approximately 220 clones were screened.

Then 13 clones with antibody titers of more than 150 µg/ml were picked and transferred to 24-well plates. The clones were expanded to shaker flasks over additional passages and subsequently transferred to serum free production medium for the final productivity assessment. A shaker flask was inoculated with 10⁵ to 10⁶ cells/ml in 50 ml medium supplemented with 200 nM MTX and 400 µg/ml G418. Viable cell density and viability were monitored over one week. Antibody titers were measured by Protein A chromatography on the final day. Based on these data, clone G24_x6 was considered the best clone. G24_x6 reached a maximal viable cell density of 3.0×10⁶ cells/ml. The antibody titer was 685 µg/ml. The average specific production rate (SPR) from was 48 pg/(cell*d).

Limiting Dilution:

To compare the method according to the invention with simple subcloning with respect to their effect on productivity we subjected clone G24 to limited dilution or single cell deposition in 96-well plates.

For limiting dilution the cells were seeded in 96-well plates in HyQ SFM4CHO medium supplemented with 50% (v/v) conditioned medium, 10% FCS and 200 nM MTX at 0.5 cells/well. Alternatively 1 cell/well was deposited in 96-well plates by FACS. After 10 days, fresh HyQ SFM4CHO medium, 200 nM MTX without FCS was added per well and after an additional week the culture medium was completely replaced by HyQ SFM4CHO medium, 200 nM MTX. Four days later the culture supernatants were tested for antibody production by anti-human Fc ELISA. In total approximately 230 clones were screened.

Eleven subclones with antibody titers of more than 130 µg/ml were transferred to 24-well plates. After passages in 6-well plates, the clones were transferred to shaker flasks and subsequently transferred to serum free production medium for the final productivity assessment. A shaker flask was inoculated with 10⁵ to 10⁶ cells/ml in medium supplemented with 200 nM MTX. Viable cell density and viability were monitored over one week. Antibody titers were measured by Protein A chromatography on the final day. Based on these data G24_13 was considered the best clone. G24_13 reached a maximal viable cell density of 3.6×10⁶ cells/ml. The antibody titer was 472 µg/ml. The average the specific production rate (SPR) was 31 pg/(cell*d).

Table 3 summarizes the productivity data of best performing subclone G24_13 and the best performing clone G24_x6 obtained with the method according to the invention in comparison to their parental clone G24. With the method according to the invention a clone with volumetric and specific productivity increased by more than 50% can be obtained whereas after subcloning only a minor increase of both parameters was observed.

Figure 6:
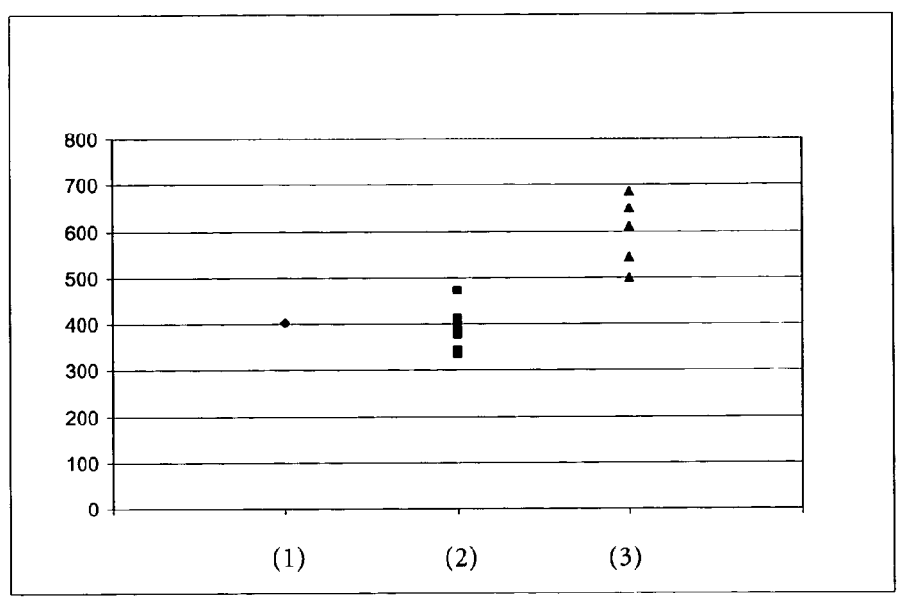
FIG. 6 (A) Antibody titers of clones obtained after subcloning with limited dilution and of clones obtained with the method according to the invention; X-axis: (1) G24, (2) limited dilution, (3) method according to the invention; Y-axis: immunoglobulin concentration [µg/ml].
Figure 6:
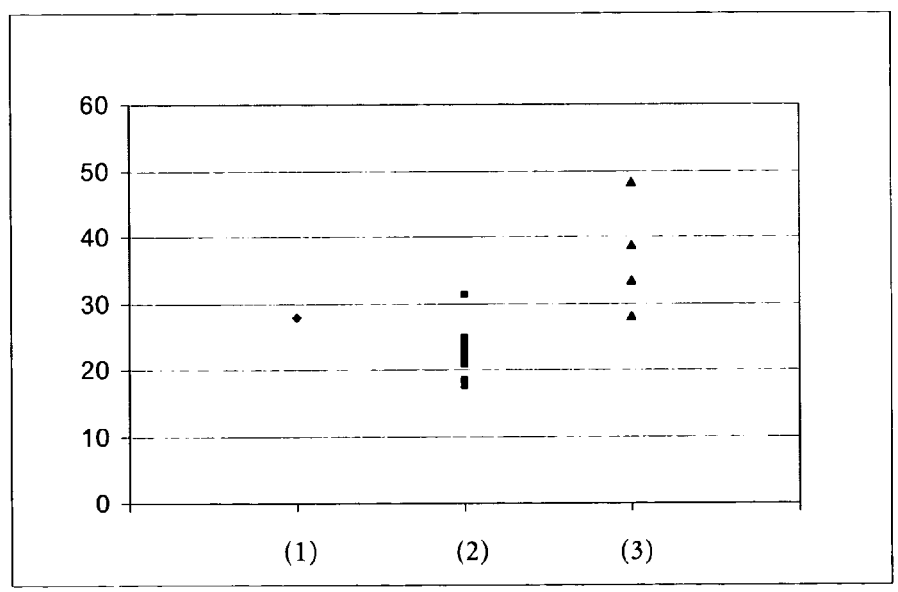

FIG. 6 shows an overview of the volumetric (A) and specific (B) productivities of all subclones of G24 that had been investigated in shake flasks. As can be seen, the average volumetric and specific productivity of the clones obtained with the method according to the invention was significantly higher than after subcloning.

TABLE 3

Productivity of the best producing clones compared to the parental clone G24.

|  | G24 | G24_13 (Subclone) | G24_x6 (method according to the invention) |
| --- | --- | --- | --- |
| Antibody concentration in the supernatant [µg/ml] | 402 | 472 | 685 |
| SPR pg/(cell*d)] | 28 | 31 | 48 |
| Max. cell density [10⁵/ml] | 33 | 36 | 30 |

Clone Characteristics:

As can be seen from the following table the doubling time and the cell density after three days of cultivation were comparable when the one-time transfected cell line G24 and the selected clones are compared.

TABLE 4

Growth characteristics

| Clone | Doubling time [h] | Starting cell density [10⁶ cells/ml] | Cell density at day 3 [10⁶ cells/ml] | Viability at day 3 [%] |
| --- | --- | --- | --- | --- |
| G24 | 29 | 0.3 | 0.7 | 91 |
| G24_13 | 27 | 0.3 | 2.0 | 91 |
| G24_x6 | 24 | 0.3 | 2.5 | 93 |

Example 6

Transfection and Selection of a CHO Cell Line Expressing an Anti-P-Selectin Antibody CHO-DG44 cells pre-adapted to growth in serum-free suspension culture in protein-free HyQ SFM4CHO medium (Hyclone, Cat. No. SH30549) were used as the host cell line. The host cell line was cultured in commercial medium HyQ SFM4CHO-utility (Hyclone, Cat. No. SH30516) during transfections, screening and subcloning steps.

First Transfection and Selection

Prior to transfection the expression plasmid 5057 (FIG. 4) was linearized within the beta-lactamase gene using the restriction enzyme PvuI.

The transfection of the host cell line was performed by nucleotransfection provided by AMAXA (Nucleofector Kit T, Cat. No. VCA-1002, Transfection program U-17). Cells were cultured in medium supplemented with 10% fetal calf serum for 48 h after transfection.

Transfected cells were plated on 96-well plates with 1000 cells per well in medium supplemented with 10% fetal calf serum in the presence of 40 nM methotrexate (MTX) as selection agent and incubated for approx. three weeks.

Antibody concentration was determined by ELISA in the supernatant of the 96-well plates. About 400 primary clones were screened. Twenty-four clones with the highest antibody productivity were transferred to 24-well plates and cultivated in the presence of the selection agent without supplementation with fetal calf serum. Product quality was analyzed by Western Blotting detecting light and heavy antibody chains. Nine clones which showed the highest productivity and which expressed antibody without detectable antibody derived side products (Western blot) were expanded into shake flasks.

Productivity was analyzed in batch shake flasks after 7 and 10 days of incubation. Product quality was assessed by SDS-PAGE after Protein-A HPLC purification (FIG. 7). Best product concentration was reached with clone 43-16. Best specific productivity per cell was achieved with clone 35-45. Both clones showed no detectable side products in the SDS-PAGE. Both clones were selected for subcloning by limiting dilution.

Parental clones 35-45 and 43-16 were subcloned by limiting dilution on 96-well plates in commercial HyQ medium supplemented with 5% (v/v) fetal calf serum in the presence of 20 nM MTX. After 20 days of incubation antibody production was screened by ELISA. Best subclones in terms of productivity were expanded to shake flasks and subsequently transferred to serum free production medium for the final productivity assessment. The two best subclones, 35-45-F2 and 43-16-A10, of the parental clones 35-45 and 43-16 were assessed in standard batch shake flask assay. Productivity was 270 µg/ml and 185 µg/ml after 7 days and 337 µg/ml and 343 µg/ml after 10 days, respectively.

Second Transfection and Selection:

Subclone 43-16-A10 was transfected with the expression vector p5069 (FIG. 5) using the nucleofection method (Amaxa Nucleofector Kit T, VCA-1002, Transfection program U-17). The second transfection was also carried out in Hyclone medium: HyQ SFM4CHO-utility (Cat. No. SH30516) supplemented with 10% fetal calf serum and 20 nM MTX. Two days after the second transfection cells were transferred to 96-well plates with 1000 cells per well. As second selection agent 250 µg/ml G418 was added.

After cultivation for two weeks more than 2000 primary wells were screened by antibody titer determination by anti-human Fc ELISA. Fifty clones with highest productivity were transferred into 24-well plates and screened a second time by anti-human Fc ELISA three days later. All clones were transferred to 6-well plates and screened by anti-human Fc ELISA three days later. The six clones with the best productivity were directly subcloned from the 6-well plate stage.

Limiting Dilution:

The best parental clones of the second transfection and selection round 43-16A10_S1, 43-16A10_S13, 43-16A10_S14, 43-16A10_S19, 43-16A10_S24, 43-16A10_S43 were subcloned by limiting dilution. The product quality of the twelve best subclones was assessed in SDS-PAGE and Western-Blotting from the 24-well stage. No unwanted antibody related side products were detected.

Three subclones, 43-16-A10-S1-16, 43-16-A10-S24-11, and 43-16-A10-S43-14, were selected according to their productivity in 6-well plates for the expansion in shake flasks. They were transferred to serum free production medium for the final productivity assessment. Their productivity was compared to the subclone after the first transfection, clone 43-16-A10. The productivity was increased twofold for two of the clones after the second transfection and selection, 43-16-A10-S1-16 and 43-16-A10-S24-11, from 221 µg/ml after 7 days in the batch shake flask to 436 µg/ml and 407 µg/ml, respectively. After 10 days incubation in the batch shake flask the productivity increased from 306 µg/ml to 683 µg/ml and 446 µg/ml, respectively.

The specific productivity per cell increased as well from 17 pg/cell/day for the clone 43-16-A10 after the first transfection to 40 pg/cell/day for the first transfected clone 43-16-A10-S1-16 and to 33 pg/cell/day for the second transfected clone 43-16-A10-S24-11. The doubling time was not affected by the second transfection. The doubling time for the clone 43-16-A10 after the first transfection was 33 h and it was 32 h for both clones 43-16-A10-S1-16 and 43-16-A10-S24-11.

Example 7

Expression Vector for Expressing an Anti-IL-13Rα Antibody

Another example (preferably monoclonal) antibody for which a cell line for expression can be obtained according to the current invention is an antibody binding to the IL-13 Receptor alpha 1 (anti-IL-13Rα1 anti-IL-13Rα antibody). Such an antibody and the corresponding nucleic acid sequences are for example described in WO 2006/072564 or SEQ ID NO: 19 to 28.

A genomic human kappa-light chain constant region gene segment (C-kappa) was added to the light chain variable region of the anti-IL-13Rα antibody whereas a human gamma 1-heavy chain constant region gene segment ($C_{H1}$-Hinge-$C_{H2}$-$C_{H3}$) was added to the heavy chain variable region of the anti-IL-13Rα antibody. The expression plasmid 5321 comprises an expression cassette for the anti-IL-13Rα antibody γ1-heavy chain, and the anti-IL-13Rα antibody κ-light chain, and a nucleic acid encoding the murine DHFR gene. An annotated plasmid map is shown in FIG. 9.

a) Heavy Chain Expression Cassette

The transcription unit of the anti-IL-13Rα antibody conjugate heavy chain is composed of the following elements:
the immediate early enhancer and promoter from the human cytomegalovirus (CMV IE),
a 5'-untranslated region (5' UTR),
the coding sequence for the anti-IL-13Rα antibody gamma 1-heavy chain conjugate including a signal peptide in an intron-exon gene structure,
the human gamma 1-immunoglobulin polyadenylation signal sequence.

b) Light Chain Expression Cassette

The transcription unit of the anti-IL-13Rα antibody light chain is composed of the following elements:
the immediate early enhancer and promoter from the human cytomegalovirus (CMV IE),
a 5'-untranslated region (5' UTR),
the coding sequence for the anti-IL-13Rα kappa-light chain in an intron-exon gene structure,
the human immunoglobulin kappa-polyadenylation signal sequence.

c) Expression Plasmids

For the expression and production of the anti-IL-13Rα antibody conjugate the light and heavy chain expression cassettes were placed on a single expression vector (light chain upstream of heavy chain). Two identical expression vectors were generated differing only in the selectable marker gene included, in particular, the murine DHFR gene and both the murine DHFR gene and a hygromycin resistance gene.

The expression vectors contain beside the light and heavy chain expression cassette the following elements:
an origin of replication allowing for the replication of the plasmid in *E. coli* (pUC origin),
a beta-lactamase gene which confers ampicillin resistance in *E. coli*.

Example 8

Transfection and Selection of a CHO Cell Line Expressing an Anti-IL-13Rα Antibody For the first transfection and selection step the plasmid 5321 has been used. Plasmid 5321 has been transfected with electroporation into parent cell line adapted to growth in ProCHO4-complete medium. The transfected cells were cultivated in HyQSFMCHO-medium (HyClone) supplemented with up to 200 nM methotrexate in plates. The antibody concentration in the culture supernatants was evaluated by an anti-human IgG1 ELISA. The clones have been tested and the selected of them were further cultivated in 24-well plates, 6-well plates and subsequently in shaker flasks. The growth and productivity was assessed in static and suspension cultures by anti-human IgG1 ELISA and/or analytic Protein A HPLC. The best clone (best clone does not denote the most productive clone it denotes the clone with the best properties for the further steps) was selected. The selected clone was named 200__019. Productivity was 90 μg/ml with an average specific production rate of 7 pg/cell*d after 7 days of cultivation.

For the second transfection and selection step a plasmid with a DHFR and hygromycin resistance gene has been used. The plasmid has been transfected with electroporation into the selected cell line cultivated in HyQSFMCHO-medium (HyClone) supplemented with up to 200 nM methotrexate. The double selection medium contained in addition 300 μg/ml hygromycine B. Single antibody secreting cells were identified and deposited on the basis of their fluorescence intensity after staining with a Protein A Alexa Fluor conjugate by FACS analysis. The selected clone was named 5__17__35. Productivity was 150 μg/ml with an average specific production rate of 10 pg/cell*d after 7 days of cultivation.

Example 9

Expression Vector for Expressing an Anti-CD4 Antibody Conjugate

Another example (monoclonal) antibody for which a cell line for expression can be obtained according to the current invention is an antibody against the human CD4 surface receptor (anti-CD4 antibody) which is conjugated to two to eight antifusogenic peptides. Such an antibody and the corresponding nucleic acid sequences are for example reported in PCT/EP2008/005894 or SEQ ID NO: 29 to 40.

A genomic human kappa-light chain constant region gene segment (C-kappa) was added to the light chain variable region of the anti-CD4 antibody of SEQ ID NO: 39, whereas a human gamma 1-heavy chain constant region gene segment ($C_{H1}$-Hinge-$C_{H2}$-$C_{H3}$) was added to the heavy chain variable region of the anti-CD4 antibody of SEQ ID NO: 36. The expression plasmid 6311 comprises an anti-CD4 antibody γ1-heavy chain, which is joint at the last but one C-terminal amino acid, i.e. the C-terminal lysine residue of the heavy chain is removed, with a nucleic acid encoding an antifusogenic peptide of SEQ ID NO: 41 via the peptidic glycine-serine linker of SEQ ID NO: 42, and a anti-CD4 antibody κ-light chain, and a nucleic acid conferring resistance to the selectable marker neomycin. An annotated plasmid map is shown in FIG. 8.

a) Heavy Chain Expression Cassette

The transcription unit of the anti-CD4 antibody conjugate heavy chain is composed of the following elements:
- the immediate early enhancer and promoter from the human cytomegalovirus (CMV IE),
- a 5'-untranslated region (5' UTR),
- the coding sequence for the anti-CD4 antibody gamma 1-heavy chain conjugate including a signal peptide in an intron-exon gene structure,
- the SV 40 early poly A signal sequence.

b) Light Chain Expression Cassette

The transcription unit of the anti-CD4 antibody conjugate light chain is composed of the following elements:
- the immediate early enhancer and promoter from the human cytomegalovirus (CMV IE),
- a 5'-untranslated region (5' UTR),
- the coding sequence for the anti-CD4 kappa-light chain in an intron-exon gene structure,
- the SV 40 early poly A signal sequence.

c) Expression Plasmids

For the expression and production of the anti-CD4 antibody conjugate the light and heavy chain expression cassettes were placed on a single expression vector (light chain upstream of heavy chain). Three identical expression vectors were generated differing only in the selectable marker gene included, in particular, a neomycin resistance gene, a puromycin resistance gene, and a hygromycin resistance gene.

The expression vectors contain beside the light and heavy chain expression cassette the following elements:
- an origin of replication allowing for the replication of the plasmid in *E. coli* taken from pUC18 (pUC origin),
- a beta-lactamase gene which confers ampicillin resistance in *E. coli*.

Example 10

Transfection and Selection of a CHO Cell Line Expressing an Anti-CD4 Antibody Conjugate Transfection and Selection Steps:

For the first transfection and selection step the plasmid 6311 has been used. Plasmid 6311 has been transfected with electroporation into parent cell line adapted to growth in ProCHO4-complete medium. The transfected cells were cultivated in ProCHO4-complete medium supplemented with up to 700 μg/ml G418 in 96 well plates. The antibody concentration in the culture supernatants was evaluated by an anti-human IgG1 ELISA. Approximately 5000 clones have been tested and the selected of them were further cultivated in 24-well plates, 6-well plates and subsequently in shaker flasks. The growth and productivity of approximately 15 clones was assessed in static and suspension cultures by anti-human IgG1 ELISA and/or analytic Protein A HPLC. The best clone (best clone does not denote the most productive clone it denotes the clone with the best properties for the further steps) was subcloned by limited dilution in ProCHO4-conditioned medium supplemented with 700 μg/ml G418.

Subclones were obtained by two methods, Limiting Dilution (LD) and Fluorescence Activated Cell Sorting (FACS).

Limiting Dilution:

For limiting dilution cells were plated out in ProCHO4-selection medium at a cell density of 0.5-2 cells per 0.1 ml medium per well of a 96-well culture plate.

Single Cell Deposition by Flow Cytometry Including Identification and Isolation of Clones:

In the case of fluorescence activated cell sorting the electroporated population of cells were directly seeded into T-flasks in ProCHO4-complete medium. The appropriate selection agent or agents (G418, hygromycin, and/or puromycin) was/were added to the culture one day after transfection and the transfectant pool was expanded. The growth and productivity of approximately 112 clones was assessed in static and suspension cultures by anti-human IgG1 ELISA and/or analytic Protein A HPLC. The selected clone was named I-17.

For the second transfection and selection step a plasmid with a hygromycin resistance gene has been used. The plasmid has been transfected with electroporation into cell line clone I-17 cultivated in ProCHO4-complete medium supplemented with 700 μg/ml G418. The transfected cells were expanded for about two to three weeks in ProCHO4-conditioned medium supplemented with 200 μg/ml G418 and 300 μg/ml hygromycin (ProCHO4-double selection medium). Single antibody secreting cells were identified and deposited on the basis of their fluorescence intensity after staining with a Protein A Alexa Fluor conjugate by FACS analysis. The deposited cells were cultivated in ProCHO4-double selection medium in 96 well plates. The antibody concentration in the culture supernatants was evaluated by an anti-human IgG1 ELISA. The selected clone was named 24_16. For the third transfection and selection step a plasmid with a puromycin resistance gene has been used. The plasmid has been transfected with electroporation into cell line clone 24_16 cultivated in ProCHO4-double selection medium. The transfected cells were expanded for about two to three weeks in ProCHO4-triple selection medium (ProCHO4-conditioned medium supplemented with 200 μg/ml G418 and 300 μg/ml hygromycin and 4 μg/ml puromycin). Single antibody secreting cells were identified and deposited on the basis of their fluorescence intensity after staining with a Protein A Alexa Fluor conjugate by FACS analysis. The deposited cells were cultivated in ProCHO4-triple selection medium in 96 well plates. The antibody concentration in the culture supernatants was evaluated by an anti-human IgG1 ELISA. The selected clone was named 1_24.

Clone Characteristics:

As can be seen from the following table the doubling time and the cell density after three days of cultivation were comparable when the basic cell line CHO-K1 (wild-type) and the selected clones are compared.

TABLE 5

Growth characteristics

| Clone | Doubling time [h] | Starting cell density [$10^6$ cells/ml] | Cell density at day 3 [$10^6$ cells/ml] | Viability at day 3 [%] |
|---|---|---|---|---|
| CHO-K1 (pre adapted) | 22-25 | 3 | 18-22 | 96-98 |
| I-17 | 25-30 | 3 | 13-15 | 95-97 |
| 24_16 | 25-30 | 3 | 15-16 | 95-96 |
| 1_24 | 30-32 | 3 | 12-14 | 95-97 |

The invention claimed is:

1. A method for the recombinant production of a heterologous immunoglobulin in a CHO cell which is secreted to the cultivation medium comprising:
   a) providing a CHO cell, wherein said CHO cell is
      adapted to growth in suspension culture,
      adapted to growth in serum-free medium, and
      mycoplasma free,
   b) providing a nucleic acid comprising
      i) a prokaryotic origin of replication,
      ii) a first nucleic acid sequence conferring resistance to a prokaryotic selection agent,
      iii) a second nucleic acid sequence encoding the heavy chain of said heterologous immunoglobulin, and a third nucleic acid sequence encoding the light chain of said heterologous immunoglobulin,
   whereby a first transfection vector is provided which comprises said provided nucleic acid and an additional fourth nucleic acid sequence conferring resistance to a first eukaryotic selection agent,
   whereby a second transfection vector is provided which comprises said provided nucleic acid and an additional fourth nucleic acid sequence conferring resistance to a second eukaryotic selection agent, whereby said second eukaryotic selection agent is different to said first eukaryotic selection agent,
   b1) providing a nucleic acid comprising
      i) a prokaryotic origin of replication,
      ii) a first nucleic acid sequence conferring resistance to a prokaryotic selection agent,
      iii) a second nucleic acid sequence encoding the heavy chain of said heterologous immunoglobulin, and/or a third nucleic acid sequence encoding the light chain of said heterologous immunoglobulin,
   whereby a third transfection vector is provided which comprises said provided nucleic acid and an additional fourth nucleic acid sequence conferring resistance to a third eukaryotic selection agent, whereby said third eukaryotic selection agent is different to said first eukaryotic selection agent and is also different to said second eukaryotic selection agent,
   c) transfecting said CHO cell, wherein said transfecting comprises the following:
      (i) transfecting said CHO cell with said first transfection vector,
      (ii) selecting a CHO cell transfected in (i) by selected growth in cultivation medium containing a first eukaryotic selection agent to which the first transfection vector confers resistance,
      (iii) transfecting said selected CHO cell in (ii) with said second transfection vector,
      (iv) selecting a CHO cell transfected in (iii) by selected growth in cultivation medium containing said first eukaryotic selection agent to which the first transfection vector confers resistance and said second eukaryotic selection agent to which the second transfection vector confers resistance,
      (v) transfecting said CHO cell selected in (iv) with said third transfection vector,
      (vi) selecting a CHO cell transfected in (v) by selected growth in a cultivation medium containing said first eukaryotic selection agent to which the first transfection vector confers resistance and said second eukaryotic selection agent to which the second transfection vector confers resistance and said third eukaryotic selection agent to which the third transfection vector confers resistance,
   d) cultivating said transfected CHO cell in a medium in the presence of said first and said second and third eukaryotic selection agent, under conditions suitable for the expression of said second, and/or third nucleic acid, and
   e) recovering said secreted heterologous immunoglobulin from the cultivation medium and thereby producing a heterologous immunoglobulin in a CHO cell which is secreted to the cultivation medium;
   wherein said resultant CHO cell is stable in the absence of any or all selection agents, as used in the previous steps, for up to generation 60.

2. The method of claim 1, wherein said CHO cell is selected from the group consisting of a CHO K1 cell, a CHO DG44 cell, a CHO XL99 cell, a CHO DXB11 cell, and a CHO DP12 cell; and wherein further the heterologous immunoglobulin is selected from the group consisting of an anti-AB antibody, an anti P-selection antibody, an anti-IL-13R or antibody and an anti-CD4 antibody conjugate.

3. The method of claim 2, wherein said second and/or third nucleic acid contains hybrid intronic nucleic acid sequence.

4. The method of claim 2, characterized in that said first transfection vector and said second transfection vector differ only in the nucleic acid conferring resistance to said eukaryotic selection agent.

5. The method of claim 2, wherein step c) and step d) are performed in the same medium.

6. The method of claim 5, wherein said medium is selected form the group consisting of a serum-free medium, a serum-free medium supplemented with defined animal-derived components, an animal-derived component free medium, a protein-free medium, a protein-free medium supplemented with defined animal-derived components, a defined protein-free medium, and a chemically defined medium.

7. The method of, claim 2, wherein the cultivating of step d) is either in the presence of the eukaryotic selection agents in a volume of less than 500 liter or said cultivating is in the absence of said eukaryotic selection agents in a volume of 500 liter or more, and that the recovering of the secreted heterologous immunoglobulin is from the cultivation medium without said eukaryotic selection agents.

8. The method of claim 2, characterized in that the productivity of said CHO cells is over 40 generations not less than 70% and not more than 130% of the productivity after 10 generations of cultivation as split-batch cultivation.

9. The method of claim 8, characterized in that the productivity of said CHO cell is at least 1.5 g/l of said heterologous immunoglobulin within 21 days as fed-batch cultivation.

10. The method of claim 1, characterized in that said method further comprises:
f) purifying said heterologous immunoglobulin with one or more chromatographic steps.

11. The method of claim 10, characterized in that said transfected CHO cell of step c) has
a doubling time of 150% or less of the doubling time of the CHO cell selected in substep (ii),
a volumetric yield of at least 125% compared to the volumetric yield of the CHO cell selected in (ii).

* * * * *